FIG. 3A

United States Patent [19]
Wasmoen et al.
[11] Patent Number: 5,820,869
[45] Date of Patent: Oct. 13, 1998
[54] RECOMBINANT RACCOON POX VIRUSES AND THEIR USE AS AN EFFECTIVE VACCINE AGAINST FELINE IMMUNODEFICIENCY VIRUS INFECTION
[75] Inventors: Terri Wasmoen; Hsien-Jue Chu, both of Fort Dodge, Iowa; Lloyd Chavez, Highlands Ranch, Colo.
[73] Assignee: American Home Products Corporation, Madison, N.J.
[21] Appl. No.: 482,090
[22] Filed: Jun. 7, 1995
[51] Int

```
         10         20         30         40         50         60
          *          *          *          *          *          *
GGATCCAACA ATAATTATGG CAGAAGGATT TGCAGCCAAT AGACAATGGA TAGGACCAGA
CCTAGGTTGT TATTAATACC GTCTTCCTAA ACGTCGGTTA TCTGTTACCT ATCCTGGTCT
              M  A  E  G  F  A  A  N  R  Q  W  I  G  P  E〉

70         80         90        100        110        120
          *          *          *          *          *          *
AGAAGCTGAA GAGTTATTAG ATTTTGATAT AGCAACACAA ATGAATGAAG AAGGGCCACT
TCTTCGACTT CTCAATAATC TAAAACTATA TCGTTGTGTT TACTTACTTC TTCCCGGTGA
 E  A  E  E  L  L  D  F  D  I  A  T  Q  M  N  E  E  G  P  L〉

130        140        150        160        170        180
          *          *          *          *          *          *
AAATCCAGGG ATGAACCCAT TTAGGGTACC TGGAATAACA GATAAAGAAA AGCAAGACTA
TTTAGGTCCC TACTTGGGTA AATCCCATGG ACCTTATTGT CTATTCTTT TCGTTCTGAT
 N  P  G  M  N  P  F  R  V  P  G  I  T  D  K  E  K  Q  D  Y〉

190        200        210        220        230        240
          *          *          *          *          *          *
TTGTAACATA TTACAACCTA AGTTACAAGA TTTACGGAAT GAACTTCAAG AGTAAAAACT
AACATTGTAT AATGTTGGAT TCAATGTTCT AAATGCCTTA CTTGAAGTTC TCATTTTTGA
 C  N  I  L  Q  P  K  L  Q  D  L  R  N  E  L  Q  E  V  K  L〉
```

FIG. 3B

```
       250        260        270        280        290        300
        *          *          *          *          *          *
AGAAGAAGGA AATGCAGGTA AGTTTAGAAG AACAAGATTT TTAAGGTATT CTGATGAACA
TCTTCTTCCT TTACGTCCAT TCAAATCTTC TTGTTCTAAA AATTCCATAA GACTACTGT
 E  E  G   N  A  G    K  F  R  R    T  R  F    L  R  Y    S  D  E  Q>

310        320        330        340        350        360
        *          *          *          *          *          *
AGTATTGTCC CCGGTTCATG CGTTCATAGG ATATTGTATT TATTTAGGTA ATCGAAATAA
TCATAACAGG GGCCAAGTAC GCAAGTATCC TATAACATAA ATAAATCCAT TAGCTTTATT
 V  L  S   P  V  H    A  F  I  G    Y  C  I    Y  L  G    N  R  N  K>

370        380        390        400        410        420
        *          *          *          *          *          *
GTTAGGATCT TTAAGACATG ACATTGATAT TGAAGCACCC CCCGAAGAGT GTTATGATAA
CAATCCTAGA AATTCTGTAC TGTAACTATA ACTTCGTGGG GGGCTTCTCA CAATACTATT
 L  G  S   L  R  H    D  I  D  I    E  A  P    P  E  E    C  Y  D  N>

430        440        450        460        470        480
        *          *          *          *          *          *
                                                AvrII
TAGAGAGAAG GGTACAACTG ACAATATAAA ATATGGTAGA CGATGTTGCC TAGGAACGGT
ATCTCTCTTC CCATGTTGAC TGTTATATTT TATACCATCT GCTACAACGG ATCCTTGCCA
 R  E  K   G  T  T    D  N  I  K    Y  G  R    R  C  C    L  G  T  V>
```

FIG. 3C

```
       490        500        510        520        530        540
        *          *          *          *          *          *
GACTTTGTAC CTGATTTTAT TTATAGGATT AATAATATAT TCACAGACAG CCGACGCTCA
CTGAAACATG GACTAAAATA AATATCCTAA TTATTATATA AGTGTCTGTC GGCTGCGAGT
  T  L  Y   L  I  L    F  I  G  L   I  I  Y    S  Q  T    A  D  A  Q>

550        560        570        580        590        600
        *          *          *          *          *          *
GGTAGTATGG AGACTTCCAC CATTAGTAGT CCCAGTAGAA GAATCAGAAA TAATTTTTTG
CCATCATACC TCTGAAGGTG GTAATCATCA GGGTCATCTT CTTAGTCTTT ATTAAAAAAC
  V  V  W   R  L  P    P  L  V  V   P  V  E    E  S  E    I  I  F  W>

610        620        630        640        650        660
        *          *          *          *          *          *
GGATTGTTGG GCACCAGAAG AACCCGCCTG TCAGGACTTT CTTGGGGCAA TGATACATCT
CCTAACAACC CGTGGTCTTC TTGGGCGGAC AGTCCTGAAA GAACCCCGTT ACTATGTAGA
  D  C  W   A  P  E    E  P  A  C   Q  D  F    L  G  A    M  I  H  L>

670        680        690        700        710        720
        *          *          *          *          *          *
AAAAGCTAAG ACAAATATAA GTATACGAGA GGGACCTACC TTGGGGAATT GGGCTAGAGA
TTTTCGATTC TGTTTATATT CATATGCTCT CCCTGGATGG AACCCCTTAA CCCGATCTCT
  K  A  K   T  N  I    S  I  R  E   G  P  T    L  G  N    W  A  R  E>
```

FIG. 3D

```
         730        740        750        760        770        780
          *          *          *          *          *          *
    AATATGGGCA ACATTATTCA AAAAGGCTAC TAGACAATGT AGAAGAGGCA GAATATGGAA
    TTATACCCGT TGTAATAAGT TTTTCCGATG ATCTGTTACA TCTTCTCCGT CTTATACCTT
      I  W  A   T  L  F    K  K  A  T    R  Q  C    R  R  G    R  I  W  K>

790        800        810        820        830        840
          *          *          *          *          *          *
    AAGATGGGAT GAGACTATAA CAGGACCATC AGGATGTGCT AATAACACAT GTTATAATGT
    TTCTACCCTA CTCTGATATT GTCCTGGTAG TCCTACACGA TTATTGTGTA CAATATTACA
      R  W  D   E  T  I    T  G  P  S    G  C  A    N  N  T    C  Y  N  V>

850        860        870        880        890        900
          *          *          *          *          *          *
    TTCAGCAATA GTACCTGATT ATCAGCGTTA TTTAGATAGA GTAGATACTT GGTTACAAGG
    AAGTCGTTAT CATGGACTAA TAGTCGCAAT AAATCTATCT CATCTATGAA CCAATGTTCC
      S  A  I   V  P  D    Y  Q  R  Y    L  D  R    V  D  T    W  L  Q  G>

910        920        930        940        950        960
          *          *          *          *          *          *
    GAAAATAAAT ATATCATTAT GTCTAACAGG AGGAAAAATG TTGTACAATA AAGTTACAAA
    CTTTTATTTA TATAGTAATA CAGATTGTCC TCCTTTTTAC AACATGTTAT TTCAATGTTT
      K  I  N   I  S  L    C  L  T  G    G  K  M    L  Y  N    K  V  T  K>
```

FIG. 3E

```
       970        980        990       1000       1010       1020
        *          *          *          *          *          *
ACAATTAAGC TATTGTACAG ACCCATTACA AATCCCACTG ATCAATTATA CATTGGACC
TGTTAATTCG ATAACATGTC TGGGTAATGT TTAGGGTGAC TAGTTAATAT GTAAACCTGG
 Q  L  S   Y  C  T    D  P  L  Q   I  P  L   I  N  Y    T  F  G  P>

1030       1040       1050       1060       1070       1080
        *          *          *          *          *          *
TAATCAAACA TGTATGTGGA ATACTTCACA AATTCAGGAC CCTGAAATAC CACAATGTGG
ATTAGTTTGT ACATACACCT TATGAAGTGT TTAAGTCCTG GGACTTTATG GTGTTACACC
 N  Q  T   C  M  W    N  T  S  Q   I  Q  D   P  E  I    P  Q  C  G>

1090       1100       1110       1120       1130       1140
        *          *          *          *          *          *
ATGGTGGAAT CACATGGCCT ATTATAAACAG TTGTAAATGG GAAGAGGCAA AGTAAAGTT
TACCACCTTA GTGTACCGGA TAATATTGTC AACATTACC CTTCTCCGTT TCCATTTCAA
 W  W  N   H  M  A    Y  Y  N  S   C  K  W   E  E  A    K  V  K  F>

1150       1160       1170       1180       1190       1200
        *          *          *          *          *          *
TCATTGTCAA AGAACACAGA GTCAGCCTGG GTCATGGCGT AGAGCAATCT CGTCATGGAA
AGTAACAGTT TCTTGTGTCT CAGTCGGACC CAGTACCGCA TCTCGTTAGA GCAGTACCTT
 H  C  Q   R  T  Q    S  Q  P  G   S  W  R   R  A  I    S  S  W  K>
```

FIG. 3F

```
          1210       1220       1230       1240       1250       1260
            *          *          *          *          *          *
   ACAAAGAAAT AGATGGGAGT GGAGACCAGA TTTTGAGAGT GAAAAGGTGA AAATATCTCT
   TGTTTCTTTA TCTACCCTCA CCTCTGGTCT AAAACTCTCA CTTTTCCACT TTTATAGAGA
    Q   R   N   R   W   E   W   R   P   D   F   E   S   E   K   V   K   I   S   L>

1270       1280       1290       1300       1310       1320
            *          *          *          *          *          *
   ACAGTGCAAT AGCACGAAAA ACCTAACCTT TGCAATGAGA AGTTCAGGAG ATTATGGAGA
   TGTCACGTTA TCGTGCTTTT TGGATTGGAA ACGTTACTCT TCAAGTCCTC TAATACCTCT
    Q   C   N   S   T   K   N   L   T   F   A   M   R   S   S   G   D   Y   G   E>

1330       1340       1350       1360       1370       1380
            *          *          *          *          *          *
   AGTAACGGGA GCTTGGATAG AGTTTGGATG TCATAGAAAT AAATCAAACC TTCATACTGA
   TCATTGCCCT CGAACCTATC TCAAACCTAC AGTATCTTTA TTTAGTTTGG AAGTATGACT
    V   T   G   A   W   I   E   F   G   C   H   R   N   K   S   N   L   H   T   E>

1390       1400       1410       1420       1430       1440
            *          *          *          *          *          *
   AGCAAGGTTT AGAATTAGAT GTAGATGGAA TGTAGGGAGT GATACCCTCGC TCATTGATAC
   TCGTTCCAAA TCTTAATCTA CATCTACCTT ACATCCCTCA CTATGGAGCG AGTAACTATG
    A   F   R   I   R   C   R   W   N   V   G   S   D   T   S   L   I   D   T>
```

FIG. 3G

```
      1450       1460       1470       1480       1490       1500
        *          *          *          *          *          *
ATGTGGAAAC ACTCCAAATG TTTCAGGTGC GAATCCTGTA GATTGTACCA TGTATTCAAA
TACACCTTTG TGAGGTTTAC AAAGTCCACG CTTAGGACAT CTAACATGGT ACATAAGTTT
 C  G  N   T  P  N    V  S  G  A   N  P  V   D  C  T    M  Y  S  N>

1510       1520       1530       1540       1550       1560
        *          *          *          *          *          *
TAAAATGTAC AAGTTTTCTT TACCAAACGG GTTTACAATG AAGGTAGATG ACCTTATTAT
ATTTACATG TTCAAAAGAA ATGGTTTGCC CAAATGTTAC TTCCATCTAC TGGAATAATA
 K  M  Y   K  F  S    L  P  N  G   F  T  M   K  V  D    D  L  I  M>

1570       1580       1590       1600       1610       1620
        *          *          *          *          *          *
GCATTTCAAT ATGCCAAAAG CTGTAGAAAT GAATAATATT GCTGGAAATT GGTCTTGTAC
CGTAAAGTTA TACGGTTTTC GACATCTTTA CTTATTATAA CGACCTTTAA CCAGAACATG
 H  F  N   M  P  K    A  V  E  M   N  N  I   A  G  N    W  S  C  T>

1630       1640       1650       1660       1670       1680
        *          *          *          *          *          *
ATCTGACTTG CCATCGTCAT GGGGGTATAT GAATTGTAAT TGCCCAAATA GTAGTAGTAG
TAGACTGAAC GGTAGCAGTA CCCCCATATA CTTAACATTA ACGGGTTTAT CATCATCATC
 S  D  L   P  S  S    W  G  Y  M   N  C  N   C  P  N    S  S  S  S>
```

FIG. 3H

```
         1690       1700       1710       1720       1730       1740
          *          *          *          *          *          *
     TTATAGTGGT ACTAAAATGG CATGTCCTAG CAATCGAGGC ATCTTAAGGA ATTGGTATAA
     AATATCACCA TGATTTTACC GTACAGGATC GTTAGCTCCG TAGAATTCCT TAACCATATT
      Y  S  G   T  K  M    A  C  P  S  N  R  G   I  L  R   N  W  Y  N>

1750       1760       1770       1780       1790       1800
          *          *          *          *          *          *
     CCCAGTAGCA GGATTACGAC AATCCTTAGA ACAGTATCAA GTTGTAAAAC AACCAGATTA
     GGGTCATCGT CCTAATGCTG TTAGGAATCT TGTCATAGTT CAACATTTTG TTGGTCTAAT
      P  V  A   G  L  R    Q  S  L  E  Q  Y  Q   V  V  K   Q  P  D  Y>

1810       1820       1830       1840       1850       1860
          *          *          *          *          *          *
     CTTACTGGTC CCAGAGGAAG TCATGGAATA TAAACCTAGA AGGAAAAGGG CAGCTATTCA
     GAATGACCAG GGTCTCCTTC AGTACCTTAT ATTTGGATCT TCCTTTTCCC GTCGATAAGT
      L  L  V   P  E  E    V  M  E  Y  K  P  R   R  K  R   A  A  I  H>

1870       1880       1890       1900       1910       1920
          *          *          *          *          *          *
     TGTTATGTTG GCTCTTGCAA CAGTATTATC TATTGCCGGT GCAGGGACGG GGGCTACTGC
     ACAATACAAC CGAGAACGTT GTCATAATAG ATAACGGCCA CGTCCCTGCC CCCGATGACG
      V  M  L   A  L  A    T  V  L  S  I  A  G   A  G  T   G  A  T  A>
```

FIG. 3I

```
            1930       1940       1950       1960       1970       1980
              *          *          *          *          *          *
      TATAGGGATG GTAACACAAT ACCACCAAGT TCTGGCAACC CATCAAGAAT CTATGGAAAA
      ATATCCCTAC CATTGTGTTA TGGTGGTTCA AGACCGTTGG GTAGTTCTTA GATACCTTTT
       I  G  M  V  T  Q  Y  H  Q  V  L  A  T  H  Q  E  S  M  E  K>

1990       2000       2010       2020       2030
              *          *          *          *          *                SpeI
      GGTGACTGAA GCCTTAGAGA TAAACAACTT AAGGTTAGTT ACATTAGAGC ATCAAGTACT
      CCACTGACTT CGGAATCTCT ATTTGTTGAA TTCCAATCAA TGTAATCTCG TAGTTCATGA
       V  T  E  A  L  E  I  N  N  L  R  L  V  T  L  E  H  Q  V  L>

2050       2060       2070       2080       2090       2100
              *          *          *          *          *          *
      AGTAATAGGA TTAAAAGTAG AAGCTATGGA AAAATTTTTA TATACAGCTT TCGCTATGCA
      TCATTATCCT AATTTTCATC TTCGATACCT TTTTAAAAAT ATATGTCGAA AGCGATACGT
       V  I  G  L  K  V  E  A  M  E  K  F  L  Y  T  A  F  A  M  Q>

2110       2120       2130       2140       2150       2160
              *          *          *          *          *          *
      AGAATTAGGA TGTAATCCAA ATCAATTTTT CTCCAAAATC CCTCTTGAGT TGTGGACAAG
      TCTTAATCCT ACATTAGGTT TAGTTAAAAA GAGGTTTTAG GGAGAACTCA ACACCTGTTC
       E  L  G  C  N  P  N  Q  F  F  S  K  I  P  L  E  L  W  T  R>
```

FIG. 3J

```
         2170       2180       2190       2200       2210       2220
          *          *          *          *          *          *
GTATAATATG ACTATAAATC AAACAATATG GAATCATCGA AATATAACTT TGGGGGAATG
CATATTATAC TGATATTTAG TTTGTTATAC CTTAGTACCT TTATATTGAA ACCCCCTTAC
 Y  N  M   T  I  N   Q  T  I  W   N  H  G   N  I  T   L  G  E  W>

2230       2240       2250       2260       2270       2280
          *          *          *          *          *          *
GTATAACCAC ACCAAAGATT TACAACCAAA GTTTTATGAA ATAATAAATGG ACATAGAACC
CATATTGGTG TGGTTTCTAA ATGTTGGTTT CAAAATACTT TATTATTACC TGTATCTTGG
 Y  N  H   T  K  D   L  Q  P  K   F  Y  E   I  I  M   D  I  E  P>

2290       2300       2310       2320       2330       2340
          *          *          *          *          *          *
AAATAATGTA CAAGGGAAAA CAGGGATACA ACAATTACCC AAGTGGGAAG ATTGGGTAAG
TTTATTACAT GTTCCCTTTT GTCCCTATGT TGTTAATGGG TTCACCCTTC TAACCCATTC
 N  N  V   Q  G  K   T  G  I  Q   Q  L  P   K  W  E   D  W  V  R>

2350       2360       2370       2380       2390       2400
          *          *          *          *          *          *
ATGGATAGGA AATATTCCAC AATATTTAAA GGGACTATTG GGAGGTATCT TGGGAATAGG
TACCTATCCT TTATAAGGTG TTATAAATTT CCCTGATAAC CCTCCATAGA ACCCTTATCC
 W  I  G   N  I  P   Q  Y  L  K   G  L  L   G  G  I   L  G  I  G>
```

FIG. 3K

```
      2410        2420        2430        2440        2450        2460
        *           *           *           *           *           *
ATTAGGAGTG  TTATTATTGA  TTTTATGTTT  ACCTACATTG  GTTGATTGTA  TAAGAAATTG
TAATCCTCAC  AATAATAACT  AAATACAAA   TGGATGTAAC  CAACTAACAT  ATTCTTTAAC
 L  G  V    L  L  L    I  L  C  L    P  T  L    V  D  C    I  R  N  C>

2470        2480        2490        2500        2510        2520
        *           *           *           *           *           *
TATCCACAAG  ATACTAGGAT  ACACAGTAAT  TGCAATGCCT  GAAGTAGAAG  GAGAAGAAAT
ATAGGTGTTC  TATGATCCTA  TGTGTCATTA  ACGTTACGGA  CTTCATCTTC  CTCTTCTTTA
 I  H  K    I  L  G     Y  T  V  I    A  M  P    E  V  E    G  E  E  I>

2530        2540        2550        2560        2570        2580
        *           *           *           *           *           *
ACAACCACAA  ATGGAATTGA  GGAGAAATGG  TAGCCAATTT  GGCATGTCTG  AAAAAGAGGA
TGTTGGTGTT  TACCTTAACT  CCTCTTTACC  ATCGGTTAAA  CCGTACAGAC  TTTTTCTCCT
 Q  P  Q    M  E  L     R  R  N  G    S  Q  F    G  M  S    E  K  E  E>

2590        2600        2610        2620        2630        2640
        *           *           *           *           *           *
GGAATGATGA  AGTATCTCAG  ACTTATTTTA  TAAGGGAGAT  ACTGTGCTAA  GTTCTTCCCT
CCTTACTACT  TCATAGAGTC  TGAATAAAAT  ATTCCCTCTA  TGACACGATT  CAAGAAGGA
 E>
```

FIG. 3L

```
     2650       2660       2670       2680       2690       2700
       *          *          *          *          *          *
TTGAGGAAGG TATGTCATAT GAATCCATTT CGAACCAAAT CAAACTAATA AAGTATGTAT
AACTCCTTCC ATACAGTATA CTTAGGTAAA GCTTGGTTTA GTTTGATTAT TTCATACATA 2710       2720       2730       2740       2750       2760
       *          *          *          *          *          *
TGTAAGGTAA AAGGAAAAGA CAAAGAAGAA GAAGAAAGAA GAAAGCTTTC AAGAGGATGA
ACATTCCATT TTCCTTTTCT GTTTCTTCTT CTTCTTTCTT CTTTCGAAAG TTCTCCTACT 2770       2780       2790       2800       2810       2820
       *          *          *          *          *          *
TGACAGAGTT AGAAGATCGC TTCAGGAAGC TATTTGGCAC GACTTCTACA ACGGGAGACA
ACTGTCTCAA TCTTCTAGCG AAGTCCTTCG ATAAACCGTG CTGAAGATGT TGCCCTCTGT 2830       2840       2850       2860       2870       2880
       *          *          *          *          *          *
GCACAGTAGA TTCTGAAGAT GAACCTCCTA AAAAAGAAAA AAGGGTGGAC TGGGATGAGT
CGTGTCATCT AAGACTTCTA CTTGGAGGAT TTTTTCTTTT TTCCCACCTG ACCCTACTCA 2890       2900       2910       2920       2930       2940
       *          *          *          *          *          *
ATTGGAACCC TGAAGAAATA GAAAGAATGC TTATGGACTA GGGACTGTTT ACGAACAAAT
TAACCTTGGG ACTTCTTTAT CTTTCTTACG AATACCTGAT CCCTGACAAA TGCTTGTTTA
```

FIG. 3M

```
         2950       2960       2970       2980       2990       3000
           *          *          *          *          *          *
    GATAAAAGGA AATAGCTAAG CATGACTCAT AGTTAAAGCG CTAGCAGCTG CTTAACCGCA
    CTATTTCCT TTATCGATTC GTACTGAGTA TCAATTTCGC GATCGTCGAC GAATTGGCGT 3010       3020       3030       3040       3050       3060
           *          *          *          *          *          *
    AAACCACATC CTATGTAAAG CTTGCTAATG ACGTATAAGT TGTTCCATTG TAAGAGTATA
    TTTGGTGTAG GATACATTTC GAACGATTAC TGCATATTCA ACAAGGTAAC ATTCTCATAT 3070       3080       3090       3100       3110       3120
           *          *          *          *          *          *
    TAACCAGTGC TTTGTGAAAC TTCGAGGAGT CTCTCCGTTG AGGACTTTCG AGTTCTCCCT
    ATTGGTCACG AAACACTTTG AAGCTCCTCA GAGAGGCAAC TCCTGAAAGC TCAAGAGGGA 3130       3140       3150       3160       3170       3180
           *          *          *          *          *          *
    TGAGGCTCCC ACAGATACAA TAAATATTTG AGATTGAACC CTGTCAAGTA TCTGTGTAAT
    ACTCCGAGGG TGTCTATGTT ATTTATAAAC TCTAACTTGG GACAGTTCAT AGACACATTA 3190       3200       3210       3220
           *          *          *          *
    CTTTTTTACC TGTGAGGTCT CGGAATCCGG GCCGAGAACT TCGCA
    GAAAAAATGG ACACTCCAGA GCCTTAGGCC CGGCTCTTGA AGCGT
```

FIG. 5A

```
         10         20         30         40         50         60
          *          *          *          *          *          *
ATGGGGAATG GACAGGGGCG AGATTGGAAA ATGGCCATTA AGAGATGTAG TAATGCTGCT
TACCCCTTAC CTGTCCCCGC TCTAACCTTT TACCGGTAAT TCTCTACATC ATTACGACGA
 M  G  N   G  Q  G  R  D  W  K   M  A  I   K  R  C  S   N  A  A>

---> p15 Matrix protein 70         80         90        100        110        120
          *          *          *          *          *          *
GTAGGAGTAG GGGGAAGAG TAAAAAATTT GGGGAAGGA ATTTCAGATG GGCCATTAGA
CATCCTCATC CCCCCTTCTC ATTTTTAAA CCCCTTCCT TAAAGTCTAC CCGGTAATCT
 V  G  V   G  G  K  S  K  K  F   G  E  G  N  F  R  W   A  I  R>

130        140        150        160        170        180
          *          *          *          *          *          *
ATGGCTAATG TATCTACAGG ACGAGAACCT GGTGATATAC CAGAGACTTT AGATCAACTA
TACCGATTAC ATAGATGTCC TGCTCTTGGA CCACTATATG GTCTCTGAAA TCTAGTTGAT
 M  A  N   V  S  T  G  R  E  P   G  D  I   P  E  T  L  D  Q  L>
```

FIG. 5B

```
     190        200        210        220        230        240
      *          *          *          *          *          *
AGGTTGGTTA TTTGCGATTT ACAAGAAAGA AGAAAAAAAT TTGGATCTTG CAAAGAAATT
TCCAACCAAT AAACGCTAAA TGTTCTTTCT TCTTTTTTTA AACCTAGAAC GTTTCTTTAA
 R  L  V   I  C  D  L   Q  E  R    R  K  K    F  G  S  C   K  E  I>

250        260        270        280        290        300
      *          *          *          *          *          *
GATAAGGCAA TTGTTACATT AAAAGTCTTT GCGGCAGTAG GACTTTTAAA TATGACAGTG
CTATTCCGTT AACAATGTAA TTTTCAGAAA CGCCGTCATC CTGAAAATTT ATACTGTCAC
 D  K  A   I  V  T  L   K  V  F    A  A  V   G  L  L  N   M  T  V>

310        320        330        340        350        360
      *          *          *          *          *          *
TCTTCTGCTG CTGCAGCTGA AAATATGTTC ACTCAGATGG GATTAGACAC TAGACCATCT
AGAAGACGAC GACGTCGACT TTTATACAAG TGAGTCTACC CTAATCTGTG ATCTGGTAGA
 S  S  A   A  A  A  E   N  M  F    T  Q  M    G  L  D  T   R  P  S>

370        380        390        400        410        420
      *          *          *          *          *          *
ATGAAAGAAG CAGGAGGAAA AGAGGAAGGC CCTCCACAGG CATTTCCTAT TCAAACAGTA
TACTTTCTTC GTCCTCCTTT TCTCCTTCCG GGAGGTGTCC GTAAAGGATA AGTTTGTCAT
 M  K  E   A  G  G  K   E  E  G    P  P  Q   A  F  P  I   Q  T  V>
```

FIG. 5C

```
                           p15 <------  ------> p25
                                        Capsid protein 430         440         450         460         470         480
      *           *           *           *           *           *
AATGGAGTAC  CACAATATGT  AGCACTTGAC  CCAAAAATGG  TGTCCATTTT  TATGGAAAAG
TTACCTCATG  GTGTTATACA  TCGTGAACTG  GGTTTTTACC  ACAGGTAAAA  ATACCTTTTC
 N  G  V    P  Q  Y  V   A  L  D    P  K  M    V  S  I  F   M  E  K>

490         500         510         520         530         540
      *           *           *           *           *           *
GCAAGAGAAG  GATTAGGAGG  TGAGGAAGTT  CAGCTATGGT  TCACTGCCTT  CTCTGCAAAT
CGTTCTCTTC  CTAATCCTCC  ACTCCTTCAA  GTCGATACCA  AGTGACGGAA  GAGACGTTTA
 A  R  E    G  L  G  G   E  E  V    Q  L  W    F  T  A  F   S  A  N>

550         560         570         580         590         600
      *           *           *           *           *           *
TTAACACCTA  CTGACATGGC  CACATTAATA  ATGGCCGCAC  CAGGGTGCGC  TGCAGATAAA
AATTGTGGAT  GACTGTACCG  GTGTAATTAT  TACCGGCGTG  GTCCCACGCG  ACGTCTATTT
 L  T  P    T  D  M  A   T  L  I    M  A  A    P  G  C  A   A  D  K>
```

FIG. 5D

```
          610        620        630        640        650        660
           *          *          *          *          *          *
GAAATATTGG ATGAAAGCTT AAAGCAACTT ACTGCAGGAT ATGATCGTAC ACATCCCCCT
CTTTATAACC TACTTTCGAA TTTCGTTGAA TGACGTCCTA TACTAGCATG TGTAGGGGGA
 E  I  L   D  E  S  L   K  Q  L   T  A  G   Y  D  R  T   H  P  P >
                                             M  I  V   H  I  P  L >

670        680        690        700        710        720
           *          *          *          *          *          *
GATGCTCCCA GACCATTACC CTATTTTACT GCAGCAGAAA TTATGGGTAT TGGATTTACT
CTACGAGGGT CTGGTAATGG GATAAAATGA CGTCGTCTTT AATACCCATA ACCTAAATGA
 D  A  P   R  P  L  P   Y  F  T   A  A  E   I  M  G  I   G  F  T >
 M  L  P   D  H  Y   P  I  L  L   Q  Q  K   L  W  V   L  D  L  L >

730        740        750        760        770        780
           *          *          *          *          *          *
CAAGAACAAC AAGCAGAAGC AAGATTTGCA CCAGCTAGGA TGCAGTGTAG AGCATGGTAT
GTTCTTGTTG TTCGTCTTCG TTCTAAACGT GGTCGATCCT ACGTCACATC TCGTACCATA
 Q  E  Q   Q  A  E  A   R  F  A   P  A  R   M  Q  C   S  V  E   H  G  I >
 K  N  N   K  Q  K   Q  D  L  H   Q  L  G   C  S  V   E  H  G  I >
```

```
        790        800        810        820        830        840
         *          *          *          *          *          *
CTCGAGGGAC TAGGAAAATT GGGCGCCATA AAAGCTAAGT CTCCTCGAGC TGTGCAGTTA
GAGCTCCCTG ATCCTTTTAA CCCGCGGTAT TTTCGATTCA GAGGAGCTCG ACACGTCAAT
 L  E  G   L  G  K  L  G  A  I   K  A  K   S  P  R  A   V  Q  L>
 S  R  D>

850        860        870        880        890        900
         *          *          *          *          *          *
AGACAAGGAG CTAAGGAAGA TTATTCATCC TTTATTGACA GATTGTTTGC CCAAATAGAT
TCTGTTCCTC GATTCCTTCT AATAAGTAGG AAATAACTGT CTAACAAACG GGTTTATCTA
 R  Q  G   A  K  E  D   Y  S  S   F  I  D   R  L  F  A   Q  I  D>

910        920        930        940        950        960
         *          *          *          *          *          *
CAAGAACAAA ATACAGCTGA AGTTAAGTTA TATTAAAAAC AGTCATTAAG CATGGCTAAT
GTTCTTGTTT TATGTCGACT TCAATTCAAT ATAAATTTTG TCAGTAATTC GTACCGATTA
 Q  E  Q   N  T  A  E   V  K  L   Y  L  K   Q  S  L  S   M  A  N>

970        980        990       1000       1010       1020
         *          *          *          *          *          *
GCTAATGCAG AATGTAAAAA GCCAATGACC CACCTTAAGC CAGAAAGTAC CCTAGAAGAA
CGATTACGTC TTACATTTTT CGGTTACTGG GTGGAATTCG GTCTTTCATG GGATCTTCTT
 A  N  A   E  C  K  K   P  M  T   H  L  K   P  E  S  T   L  E  E>
```

FIG. 5G

```
      1210       1220       1230       1240       1250       1260
        *          *          *          *          *          *
AAACCTGGTC ATGTAGCTGC CAAATGTTGG CAAGGAAATA GAAAGAATTC GGGAAACTGG
TTTGGACCAG TACATCGACG GTTTACAACC GTTCCTTTAT CTTTCTTAAG CCCTTTGACC
 K  P  G   H  V  A  A   K  C  W   Q  G  N   R  K  N  S   G  N  W>

1270       1280       1290       1300       1310       1320
        *          *          *          *          *          *
AAGGCGGGGC GAGCTGCAGC CCCAGTGAAT CAAGTGCAGC AAGCAGTAAT GCCATCTGCA
TTCCGCCCCG CTCGACGTCG GGGTCACTTA GTTCACGTCG TTCGTCATTA CGGTAGACGT
 K  A  G   R  A  A  A   P  V  N   Q  V  Q   Q  A  V  M   P  S  A>

1330       1340       1350
        *          *          *
CCTCCAATGG AGGAGAAACT ATTGGATTTA TAA
GGAGGTTACC TCCTCTTTGA TAACCTAAAT ATT
 P  P  M   E  E  K  L   L  D  L> p10 ----->
```

| Cat ID | Vaccination Route | Pre Challenge Viremia * | Pre Challenge CD4:CD8 | 1 Month Post Challenge Viremia * | 1 Month Post Challenge CD4:CD8 | 3 Months Post Challenge Viremia * | 3 Months Post Challenge CD4:CD8 | 9 Months Post Challenge Viremia * | 9 Months Post Challenge CD4:CD8 |
|---|---|---|---|---|---|---|---|---|---|
| RCNV-FIV gag Vaccinates | | | | | | | | | |
| AQC3 | SC | NEG | 2.70 | NEG | 1.82 | POS | 0.30 | NA | 0.61 |
| AQD4 | SC | NEG | 3.62 | NEG | 1.71 | POS | 2.18 | POS | 1.18 |
| ATF1 | SC | NEG | 3.80 | NEG | 3.87 | POS | 1.08 | POS | 1.12 |
| ATH3 | SC | NEG | 1.93 | NEG | 3.26 | POS | 0.40 | DEAD | 0.94 |
| ATI1 | SC | NEG | 3.23 | NEG | 2.17 | POS | 1.12 | POS | 0.86 |
| AQE4 | IM | NEG | 3.37 | NEG | 2.95 | POS | 1.24 | NEG | 1.19 |
| AQT4 | IM | NEG | 1.59 | NEG | 3.68 | POS | 1.44 | NA | 0.79 |
| AQY4 | IM | NEG | 2.41 | NEG | 3.86 | POS | 0.64 | POS | 0.77 |
| ATI2 | IM | NEG | 3.63 | NEG | 3.28 | POS | 1.49 | POS | 1.67 |
| ATJ1 | IM | NEG | 3.27 | NEG | 3.73 | POS | 1.05 | POS | 1.11 |
| RCNV-FIV envAB Vaccinates | | | | | | | | | |
| ARB4 | SC | NEG | 2.72 | NEG | 2.12 | NEG | 2.27 | NEG | 1.65 |
| ARO2 | SC | NEG | 3.20 | NEG | 2.26 | POS | 0.67 | POS | 1.18 |
| ATJ4 | SC | NEG | 2.16 | NEG | 2.54 | POS | 0.60 | POS | 0.76 |
| ATK1 | SC | NEG | 3.06 | NEG | 2.27 | POS | 0.90 | POS | 0.74 |
| ATL1 | SC | NEG | 2.32 | POS | 3.46 | POS | 1.16 | POS | 1.44 |
| ARD4 | IM | NEG | 3.04 | POS | 2.29 | POS | 1.07 | POS | 1.04 |
| ARE4 | IM | NEG | 2.20 | POS | 2.89 | POS | 1.23 | POS | 1.00 |
| ARG4 | IM | NEG | 2.48 | NEG | 2.79 | POS | 1.25 | NA | 1.02 |
| ATL2 | IM | NEG | 3.44 | POS | 2.63 | POS | 1.16 | POS | 1.04 |
| ATL3 | IM | NEG | 2.44 | NEG | 3.14 | POS | 1.30 | POS | 1.06 |

RCNV-FIV envAB + RCNV-FIV gag Vaccinates

| | | | | | | | | |
|---|---|---|---|---|---|---|---|---|
| ARN4 | SC | NEG | 3.04 | NEG | 2.73 | NEG | 1.88 | POS | 1.11 |
| AR02 | SC | NEG | 3.14 | POS | 3.09 | POS | 0.41 | POS | 0.51 |
| AR03 | SC | NEG | 2.76 | NEG | 4.11 | POS | 0.77 | POS | 0.74 |
| ATL4 | SC | NEG | 2.55 | NEG | 3.43 | NEG | 0.80 | POS | 0.88 |
| ATM1 | SC | NEG | 3.78 | NEG | 2.57 | POS | 0.67 | POS | 0.81 |

Wild Type RCNV Vaccinates (Controls)

| | | | | | | | | |
|---|---|---|---|---|---|---|---|---|
| ARQ4 | SC | NEG | 2.87 | NEG | 2.54 | NEG | 0.55 | POS | 0.86 |
| ARR4 | SC | NEG | 2.29 | POS | 1.93 | POS | 0.77 | POS | 0.70 |
| ATM2 | SC | NEG | 2.64 | NEG | 1.69 | POS | 0.92 | POS | 0.93 |
| ATM3 | SC | NEG | 3.91 | POS | 2.90 | POS | 0.62 | POS | 0.78 |
| ATN1 | SC | NEG | 3.01 | POS | 3.62 | POS | 1.09 | POS | 0.99 |

NA = Not Available due to Contaminated Culture

* Viremia Detected by Culture Isolation of FIV from Peripheral Blood Mononuclear Cells CD4:CD8 = Ratio of CD4 Positive Lymphocytes to CD8 Positive Lymphocytes as Measured by Flow Cytometry SC = Subcutaneous Vaccination IM = Intramuscular Vaccination

FIG. 10

| Time Point After Challenge | Group | % of Cats Viremic | Preventable Fraction¥ | % of Cats CD4:CD8 <1.0 | Preventable Fraction¥ |
|---|---|---|---|---|---|
| 1 Months | Controls | 60% | | 0% | |
| | RCNV-FIV gag | 0% | 100% | 0% | NA |
| | RCNV-FIV envAB | 40% | 33% | 0% | NA |
| | RCNV-FIV gag + envAB | 20% | 67% | 0% | NA |
| 3 Months | Controls | 80% | | 80% | |
| | RCNV-FIV gag | 100% | 0% | 30% | 63% |
| | RCNV-FIV envAB | 90% | 0% | 30% | 63% |
| | RCNV-FIV gag + envAB | 60% | 25% | 40% | 50% |
| 9 Months | Controls | 100% | | 100% | |
| | RCNV-FIV gag | 86% | 14% | 50% | 50% |
| | RCNV-FIV envAB | 89% | 11% | 20% | 80% |
| | RCNV-FIV gag + envAB | 100% | 0% | 80% | 20% |

¥Preventable Fraction = [(% Controls with Sign) − (% Vaccinates with Sign)] ÷ (% Controls with Sign) × 100

FIG. 11A

| Cat ID | Vaccination Route | Depression | Ocular Discharge | Nasal Discharge | Dyspnea | Fever | Total Score |
|---|---|---|---|---|---|---|---|
| RCNV-FIV Gag Vaccinates | | | | | | | |
| AQC3 | SC | 0 | 0 | 0 | 0 | 8 | 8 |
| AQD4 | SC | 1 | 0 | 0 | 0 | 5 | 6 |
| ATF1 | SC | 0 | 0 | 0 | 0 | 2 | 2 |
| ATH3 | SC | DEAD | DEAD | DEAD | DEAD | DEAD | DEAD |
| ATI1 | SC | 0 | 0 | 1 | 8 | 4 | 13 |
| AQE4 | IM | 0 | 1 | 1 | 28 | 5 | 35 |
| AQT4 | IM | 0 | 1 | 2 | 0 | 2 | 5 |
| AQY4 | IM | 0 | 0 | 0 | 0 | 7 | 7 |
| ATI2 | IM | 0 | 1 | 0 | 0 | 3 | 4 |
| ATJ1 | IM | 0 | 0 | 0 | 0 | 3 | 3 |
| Average | | 0.1 | 0.3 | 0.4 | 4.0 | 4.3 | 9.2 |
| %Reduction | | 0% | 86% | 0% | 55% | 0% | 41% |

FIG. 11B

| RCNV-FIV envAB Vaccinates | | | | | | |
|---|---|---|---|---|---|---|
| ARB4 | SC | 0 | 0 | 0 | 0 | 15 | 15 |
| ARO2 | SC | 0 | 0 | 1 | 4 | 1 | 6 |
| ATJ4 | SC | 0 | 0 | 0 | 4 | 5 | 9 |
| ATK1 | SC | 0 | 1 | 0 | 0 | 7 | 8 |
| ATL1 | SC | 0 | 0 | 0 | 4 | 0 | 4 |
| ARD4 | IM | 0 | 0 | 0 | 0 | 1 | 1 |
| ARE4 | IM | 0 | 0 | 0 | 0 | 0 | 1 |
| ARG4 | IM | 0 | 0 | 0 | 12 | 0 | 12 |
| ATL2 | IM | 0 | 1 | 0 | 0 | 9 | 9 |
| ATL3 | IM | 0 | 0 | 0 | 0 | 0 | 1 |
| Average | | 0.0 | 0.2 | 0.1 | 2.4 | 3.9 | 6.6 |
| %Reduction | | 0% | 92% | 75% | 73% | 3% | 58% |

| Wild Type RCNV Vaccinates (Controls) | | | | | | |
|---|---|---|---|---|---|---|
| ARQ4 | SC | 0 | 2 | 0 | 0 | 0 | 2 |
| ARR4 | SC | 0 | 0 | 0 | 0 | 12 | 12 |
| ATM2 | SC | 0 | 1 | 1 | 12 | 0 | 14 |
| ATM3 | SC | 0 | 9 | 1 | 32 | 7 | 49 |
| ATN1 | SC | 0 | 0 | 0 | 0 | 1 | 1 |
| Average | | 0.0 | 2.4 | 0.4 | 8.8 | 4.0 | 15.6 |

RECOMBINANT RACCOON POX VIRUSES AND THEIR USE AS AN EFFECTIVE VACCINE AGAINST FELINE IMMUNODEFICIENCY VIRUS INFECTION

FIELD OF THE INVENTION

The present invention pertains to the prophylaxis of disease caused by feline immunodeficiency virus (FIV), using as vaccines recombinant raccoon poxviruses (RRPVs) expressing the gag and envelope proteins of FIV.

BACKGROUND OF THE INVENTION

Feline immunodeficiency virus (FIV) infection is a significant health problem for domestic cats around the world. As in its human counterpart, infection with FIV causes a progressive disruption in immune function. In the acute phase of infection, the virus causes transient illness associated with symptoms such as lymphadenopathy, pyrexia, and neutropenia. Subsequently, an infected animal enters an asymptomatic phase of 1–2 years before clinical manifestations of immune deficiency become apparent, after which the mean survival time is usually less than one year.

FIV is a typical retrovirus that contains a single-stranded polyadenylated RNA genome, internal structural proteins derived from the gag gene product, and a lipid envelope containing membrane proteins derived from the env gene product (Bendinelli et al., *Clin.Microbiol.Rev.* 8:87, 1995). The gag gene is translated into a primary product of about 50 kDa that is subsequently cleaved by a viral protease into the matrix, capsid, and nucleocapsid proteins. The env gene yields a primary translation product of 75–80 kDa (unglycosylated molecular weight); in infected cells, the precursor has an apparent molecular weight of 145–150 kDa due to N-linked glycosylation. The env precursor is cleaved in the Golgi apparatus into the SU and TM proteins (also designated gp95 and gp40, respectively).

Most vaccines against FIV have failed to induce protective immunity. Ineffective vaccines have involved inactivated whole virus, fixed infected cells, recombinant CA and SU proteins, and a synthetic peptide corresponding to the V3 region of SU. In some cases, the vaccine actually enhanced infection after challenge. In one system, vaccination with paraformaldehyde-fixed virus or infected cells resulted in protective immunity (Yamamoto et al., *J. Virol.* 67:601, 1993), but application of this approach by others was unsuccessful (Hosie et al., in *Abstracts of the International Symposium on Feline Retrovirus Research*, 1993, page 50).

Thus, there is a need in the art for an effective vaccine against FIV that utilizes the gag or env proteins, or fragments therefrom, as immunogens.

SUMMARY OF THE INVENTION

The present invention pertains to the prevention or lessening of disease in cats caused by Feline Immunodeficiency Virus (FIV). Prevention or lessening of disease is understood to mean the amelioration of any symptoms, including immune system disruptions, that result from FIV infection.

The invention provides recombinant raccoon poxviruses having at least one internal gene comprising a DNA sequence that encodes FIV gag protein (gag), FIV envelope protein (env), a polypeptide consisting of amino acids 1–735 of FIV env, or immunogenic fragments of any of the foregoing. By immunogenic fragment is meant any portion of the coding sequence of FIV gag or env polypeptides that induces a beneficial immune response in cats.

In another aspect, the invention encompasses vaccines that comprise one or more of the FIV-expressing recombinant raccoon poxviruses described above, with a pharmaceutically acceptable carrier or diluent and a pharmaceutically acceptable adjuvant.

In yet another aspect, the invention provides methods for preventing or lessening disease caused by FIV, which is carried out by administering to a feline in need of such treatment the vaccines described above.

BRIEF DESCRIPTION OF THE DRAWINGS

FIGS. 3A–3M show the DNA [SEQ. I.D. NO. 14] and protein [SEQ. I.D. NO. 12] sequence of the env gene of FIV.

FIGS. 9A and 9B are a table illustrating the detection of viremia and CD4:CD8 ratios in vaccinated and unvaccinated cats after FIV challenge.

FIG. 10 is a table illustrating the preventable fraction for viremia and CD4:CD8 ratio changes in vaccinated and unvaccinated cats following FIV challenge.

FIGS. 11A and 11B are a table illustrating the clinical scores of vaccinated and unvaccinated cats after challenge with *Toxoplasma gondii*.

DETAILED DESCRIPTION OF THE INVENTION

Figure 1A:
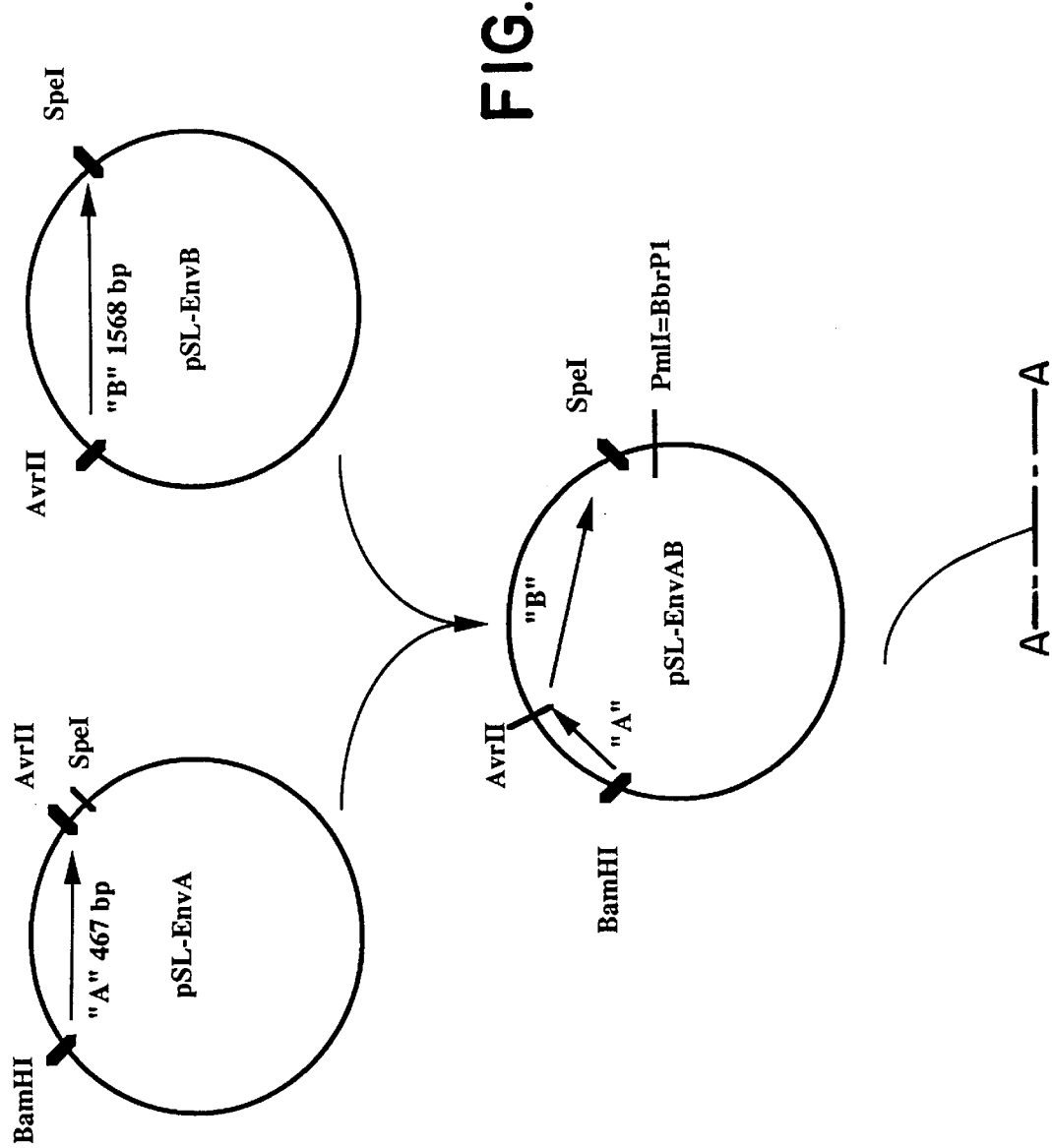
FIG. 1A and 1B are a graphic illustration of the cloning strategy for the envelope gene of FIV.

All patents, patent applications, and references cited herein are hereby incorporated by reference in their entirety. In the case of inconsistencies, the present disclosure, including definitions, will control.

The vaccine of the present invention may be prepared by creating recombinant raccoon poxviruses (RRPVs) containing a gene encoding the gag or env proteins of Feline Immunodeficiency Virus (FIV) or immunogenic fragments thereof. Gag and env genes useful in practicing the present invention may be obtained by methods well-known in the art. In one embodiment, viral RNA is reverse-transcribed using endogenous or exogenous reverse transcriptase and the DNA is rendered double-stranded using DNA polymerase. The gag and env-encoding DNA segments are then recovered by restriction enzyme digestion and are amplified by cloning in *E. coli*. In another embodiment, FIV-infected cat cells serve as a source of FIV proviral DNA. In this embodiment, chromosomal DNA is isolated from the cells, and oligonucleotide primers are used to specifically amplify the gag and env genes or fragments therefrom using polymerase chain reaction techniques. This approach is broadly applicable to purifying gag and env genes from different FIV strains or isolates, since primers can be designed from non-polymorphic regions of the FIV genome.

FIV gag and env genes isolated by the above methods are first inserted into a transfer plasmid, and the recombinant plasmid is introduced into appropriate host cells that have been previously infected with a raccoon poxvirus. As a result, the DNA from the transfer plasmid is incorporated into the poxvirus DNA by homologous recombination, producing the RRPVs that are released from the cells.

DNA encoding the FIV gag or env proteins or fragments therefrom are inserted into a transfer plasmid downstream of a poxvirus promoter. In a preferred embodiment, the early/late 7.5 kD protein promoter of vaccinia virus is used. However, alternate promoter elements could be used.

The preferred transfer plasmid also contains a beta-galactosidase marker gene, which allows for selection and detection of the plasmid DNA sequences in recombinant viruses. It will be understood by those of ordinary skill in the art that alternate selectable marker genes, such as the neomycin resistance gene or the *E. coli* gpt gene or others, could be used to practice the invention. Flanking the inserted FIV gene and the selectable marker gene are thymidine kinase DNA sequences, which facilitate integration of the plasmid DNA sequences into the raccoon poxvirus DNA by homologous recombination.

Recombinant viruses expressing the FIV gag or env genes are prepared by first infecting a susceptible cell line (such as Vero [ATCC CCL 81], BSC-1 [ATCC CCL 26], RAT-2 [ATCC CRL 1764], or CRFK [ATCC CCL 94]) with wild type raccoon poxvirus (ATCC VR-838 or similar isolates). Transfer plasmid DNA containing the FIV gag or env gene is then transfected into the infected cells using cationic liposome-mediated transfection, or other suitable techniques such as electroporation or calcium-phosphate precipitation. Raccoon poxviruses incorporate DNA from the transfer plasmid through homologous recombination with the thymidine kinase gene sequences present on the plasmid. Virus infection is allowed to proceed until cytopathic effects are noted in all cells.

Incorporation of the FIV gag or env gene into poxvirus DNA is accompanied by disruption of the viral thymidine kinase gene. Thus, recombinant virus may be selected for by the absence of a thymidine kinase gene; this is achieved by selective expansion on RAT-2 cells (tk-, ATCC CRL 1764) in the presence of 5-bromodeoxyuridine. Viruses containing a gene insert from the transfer plasmid are identified by blue plaque color when grown in the presence of a chromogenic substrate for beta-galactosidase such as X-gal.

Viral plaques that survive these selection and screening procedures are then subjected to several cycles of plaque purification. Subsequently, the presence of the gag or env genes is confirmed by polymerase chain reaction technology, and the presence of gag or env antigenic determinant is confirmed by immunoblot analysis using specific antibodies. These viruses are designated by RRPV-FIV gag and RRPV-FIV env, respectively.

In a further embodiment of the present invention, RRPVs can be produced that express less-than-full-length segments of the FIV gag and env proteins. The techniques used to engineer transfer plasmids encoding partial sequences of env and gag are well-known and widely used in the art, as are the methods for production and screening of RRPVs as detailed in this specification. For example, convenient restriction enzyme recognition sites can be used to obtain fragments of either gene, as described, e.g., Example 1 below. Alternatively, introduction of oligonucleotides containing a stop codon at various points along gag or env DNA will produce a nested set of carboxyterminal-truncated versions of that gene, which can then be incorporated into RRPVs. Furthermore, sequences that encode different domains on each protein may be recombined, using domains derived from different FIV strains or isolates. It will be apparent to one of ordinary skill in the art that systematic screening of such recombinant RRPVs can establish whether the intact protein, subfragments thereof or multi-strain recombinants thereof, are most preferred in practicing the present invention. Furthermore, as stated above, DNA encoding different fragments of gag and env can be used in a combination vaccine after incorporation into the same, or different, RRPVs.

For vaccine preparation, susceptible cells are grown in minimum essential media containing fetal bovine serum or a suitable media substitute. Cells are infected with recombinant raccoon poxvirus at a multiplicity of infection of 0.1 infectious units/cell or less. In this specification an infectious unit is defined as a Tissue Culture Infectious Dose ($TCID_{50}$), an amount of virus yielding 50% infection under defined conditions. When cytopathology is noted in >90% of the cells, the infected cells and extracellular fluids are harvested. The virus may be stored frozen (-50° C. or colder) or lyophilized until the time of use. Compounds such as NZ-amine, dextrose, gelatin or others designed to stabilize the virus during freezing and lyophilization may be added. The virus may be concentrated using commercially available equipment.

Typically, the concentration of virus in the vaccine formulation will be a minimum of $10^{6.5}$ $TCID_{50}$ per dose, but will typically be in the range of $10^{7.0}$ to $10^{9.0}$ $TCID_{50}$ per dose. At the time of vaccination, the virus is thawed (if frozen) or reconstituted (if lyophilized) with a physiologically-acceptable carrier such as deionized water, saline, phosphate buffered saline, or the like.

In one embodiment, a physiologically acceptable adjuvant such as, for example, EMA31, Adjuvant A, or combinations thereof, is added to the vaccine formulation. Non-limiting examples of suitable adjuvants include squalane and squalene (or other oils of animal origin); block copolymers such as Pluronic® (L121) Saponin; detergents such as Tween®-80; Quil® A, mineral oils such as Drakeol® or Marcol®, vegetable oils such as peanut oil; Corynebacterium-derived adjuvants such as corynebacterium parvum; Propionibacterium-derived adjuvants such as Propionibacterium acne; *Mycobacterium bovis* (Bacillus Calmette and Guerinn, or BCG); interleukins such as interleukin 2 and interleukin-12; monokines such as interleukin 1; tumor necrosis factor; interferons such as gamma interferon; combinations such as saponin-aluminum hydroxide or Quil®-A aluminum hydroxide; liposomes; iscom adjuvant; mycobacterial cell wall extract; synthetic glycopeptides such as muramyl dipeptides or other derivatives; Avridine; Lipid A; dextran sulfate; DEAE-Dextran or DEAE-Dextran with aluminum phosphate; carboxypolymethylene, such as Carbopol®; EMA; acrylic copolymer emulsions such as Neocryl® A640 (e.g. U.S. Pat. No. 5,047,238); vaccinia or animal poxvirus proteins; subviral particle adjuvants such as orbivirus; cholera toxin; dimethyldiocledecylammonium bromide; or mixtures thereof.

EMA 31 (Monsanto, St. Louis, Mo.) is a linear ethylene/maleic copolymer with approximately equal amounts of ethylene and maleic anhydride, having an estimated average molecular weight of about 75,000 to 100,000. Adjuvant A is an adjuvant comprising a block copolymer, such as a polyoxypropylene-polyoxyethylene (POP-POE) block copolymer, preferably Pluronic® L121 (e.g. U.S. Pat. No.

4,772,466), and an organic component, such as a metabolizable oil, e.g. an unsaturated turpin hydrocarbon, preferably squalane (2,6,10,15,19,23-hexamethyltetracosane) or squalene. The vaccine may also include a non-ionic detergent or surfactant, preferably a polyoxyethylene sorbitan monooleate such as a Tween® detergent, most preferably Tween®-80, i.e. polyoxyethylene (20) sorbitan monooleate.

In this adjuvant mixture, the block copolymer, organic oil, and surfactant may be present in amounts ranging from about 10 to about 40 ml/L, about 20 to about 80 ml/L, and about 1.5 to about 6.5 ml/L, respectively. In a preferred embodiment of the stock adjuvant, the organic component is squalane present in an amount of about 40 mL/L, the surfactant is polyoxyethylenesorbitan monooleate (Tween®-80) present in an amount of about 3.2 ml/L, and the POP-POE block copolymer is Pluronic® L121 present in an amount of about 20 ml/L. Pluronic® L121 is a liquid copolymer at 15°–40° C., where the polyoxypropylene (POP) component has a molecular weight of 3250 to 4000 and the polyoxyethylene (POE) component comprises about 10–20%, preferably 10%, of the total molecule.

Individual raccoon poxviruses expressing the gag or env genes may be mixed together for vaccination. Furthermore, the virus may be mixed with additional inactivated or attenuated viruses, bacteria, or fungi, or with immunogens derived from viruses, bacteria, or fungi such as feline leukemia virus, feline panleukopenia virus, feline rhinotracheitis virus, feline calicivirus, feline infectious peritonitis virus, feline *Chlamydia psittaci, Microsporum canis*, or others. In addition, antigens from the above-cited organisms may be incorporated into combination vaccines. These antigens may be purified from natural sources or from recombinant expression systems, or may comprise individual subunits of the antigen or synthetic peptides derived therefrom.

In a further embodiment of the present invention, live or inactivated RRPV virus-cell lysates can be incorporated into liposomes, or encapsulated in peptide-, protein-, or polysaccharide-based microcapsules prior to administration, using means that are known in the art. The vaccine of the present invention is administered to cats in volumes ranging from 0.5 to 5 milliliters. The vaccine can be administered to cats by subcutaneous, intramuscular, oral, intradermal, or intranasal routes. The number of injections and their temporal spacing may be varied. One to three vaccinations administered at intervals of one to three weeks are usually effective.

The efficacy of the vaccines of the present invention is assessed by the following methods. At about one month after the final vaccination, vaccinates and controls are each challenged with 3–20 cat $ID_{50}$ units, preferably 5 cat $ID_{50}$ units of FIV, preferably the NCSU1 isolate (ATCC VR-2333). Whole blood is obtained from the animals immediately before challenge, and at intervals after challenge, for measurement of a) viremia and b) relative amounts of CD4 and CD8 lymphocytes.

Viremia is measured by isolating mononuclear cells from the blood, and co-culturing the cells with mononuclear cells from uninfected animals. After 7 days of culture, the culture supernatants are tested for FIV by enzyme-linked immunoassay (See Example 5 below).

The ratio of CD4 to CD8 lymphocytes in the circulation of vaccinates and controls is taken as a measure of immune function. Typically, FIV infection causes an inversion of the normal CD4:CD8 ratio of about 1.5–4.0 to a pathological ratio of about 0.5–1.0. The numbers of CD4 and CD8 lymphocytes are measured by flow cytometry using specific antibodies (see Example 5 below).

Another measure of immune function is to challenge vaccinates and controls with *Toxoplasma gondii* at 6–12 months after the final RRPV-FIV vaccination. Normally, the severity of *T. gondii*-induced disease symptoms is considerably exacerbated in FIV-infected cats relative to uninfected cats. The severity of the *T. gondii* effect is determined by scoring ocular discharge, nasal discharge, dyspnea, and fever.

It will be understood that amelioration of any of the symptoms of FIV infection is a desirable clinical goal. This includes a lessening of the dosage of medication used to treat FIV-induced symptoms.

The following examples are intended to illustrate the present invention without limitation thereof.

EXAMPLE 1

Cloning of FIV gag and env Genes

A. Isolation of Viral DNA

FIV strain NCSU-1 (designated "FIV-NCSU-1") was isolated from a naturally infected, feline leukemia virus-negative cat and has been described previously (Tompkins et al., *J. Am. Vet. Med. Assoc.* 199: 1311, 1991. The virus was passed in a normal specific pathogen-free (SPF) cat (obtained from Liberty Laboratories, Waverly, N.Y.). FIV-infected peripheral blood mononuclear cells (PBMC) were obtained from whole blood by separation on discontinuous percoll gradients. Briefly, anti-coagulated whole blood was layered over a two step gradient containing 43% Percoll™ (Pharmacia, Piscataway, N.J.) over 62.5% Percoll™ in 0.15M NaCl. Gradients were centrifuged at 400×g for 5 minutes, followed by 800×g for 20 minutes at 22° C. PBMC were harvested from the gradient interface and washed in phosphate buffered saline containing 5% fetal bovine serum. In parallel, PBMCs were isolated from normal cats.

FIV was propagated by co-culture of PBMCs from an FIV-infected cat with PBMCs from normal cats. The cells were maintained in RPMI 1640 media containing 10% fetal bovine serum, $2.5\times10^{-5}$ beta-mercaptoethanol, 2 mM L-glutamine, 5 $\mu$g/mL concanavalin A, and 20% conditioned media from MLA cells (ATCC TIB 201) as a source of interleukin-2 (IL-2).

Cat genomic DNA containing FIV-NCSU-1 proviral sequences was isolated from the cultured PBMCs by lysis of the cells with 0.6% sodium dodecyl sulfate (SDS) in 10 mM Tris-HCl, pH 7.5, 10 mM EDTA, followed by precipitation of chromosomal DNA by incubation overnight with 1 mM NaCl. The DNA was recovered by centrifugation at 10,000 r.p.m. (Beckman J2, JA-20 rotor) for 40 minutes. The DNA pellet was resuspended in a solution containing 10 mM Tris-HCl pH 7.5, 10 mM EDTA, 0.1% SDS buffer and digested with ribonuclease A (20 $\mu$g/ml) and proteinase K (0.2 mg/ml) at 50° C. for 4 hours. DNA was then purified by sequential extraction with phenol, phenol:chloroform (1:1) and chloroform, and was recovered in pure form followed by ethanol precipitation.

B. Cloning of FIV Envelope Gene

FIV-NCSU-1 envelope DNA sequences were cloned using polymerase chain reaction (PCR) methods as follows:

Envelope Fragment A

The following oligonucleotides were used to amplify the 5' proximal segment of the env gene.

5'-TCGGATCCAACAATAATTATGGCAGAAGG-3' [SEQ. I.D. NO. 1] (Coding strand, 6252-V)

5'-AATCAGGTACAAAGTCACCGTTC-3' [SEQ. I.D. NO. 2] (Complementary strand, 6745-C)

Primer 6252-V corresponds to nucleotides 6252–6273 of FIV strain PPR (GenBank No. M36968) and primer 6745-C (underlined region) corresponds to nucleotides 6723–6745 of FIV strain 14 (GenBank No. 25381). The start codon for envelope protein translation is included in primer 6252-V. Primer 6252-V also has a synthetic BamHI restriction enzyme site near the 5' end to facilitate cloning. An AvrII site located at position 6719 also facilitates cloning. Envelope fragment A is 494 bp in length.

Envelope Fragment B

The following oligonucleotides were used to amplify the middle segment of the env gene.

5'-TATAGAAGCACCCCAAGAAGAG-3' [SEQ. I.D. NO. 3] (Coding strand, 6637-V)

5'-CATTCCCCCAAAGTTATATTTC-3' [SEQ. I.D. NO. 4] (Complementary strand, 8469-C)

Primers 6637-V and 8469-C correspond to nucleotides 6637–6659 and 8448–8469 of FIV 14 strain, respectively. An AvrII site at position 6719 and a SpeI site at position 8288 facilitated cloning. Envelope fragment B is 1833 bp in length.

Envelope Fragment C

The following oligonucleotides were used to amplify the 3' distal fragment of the env gene.

5'-TTAGTTACATTAGAGCATCAAG-3' [SEQ. I.D. NO. 5] (Coding strand, 8264-V)

5'-TTCTAGATCTTCAGGGTCCCAATACTC-3' [SEQ. I.D. NO. 6] (Complementary strand, 9145-C)

Primer 8264-V corresponds to nucleotides 8264–8285 of FIV strain 14, and primer 9145-C (underlined region) corresponds to nucleotides 9126–9145 of FIV strain PPR. Primer 9145-C has a synthetic BglII site near the 5' end to facilitate cloning. An SpeI site located at position 8288 also facilitated cloning. Envelope fragment C is 880 bp in length.

In each case, PCR was performed for 35 cycles of 1 min 30 sec at 94° C., 2 min at 56° C., and 2 min at 72° C., followed by one cycle of 8 min at 72° C. Each envelope fragment was isolated by gel electrophoresis and cloned into plasmid pSL1190 using standard methods (Maniatis et al., *Molecular Cloning: A Laboratory Manual,* 1982, Cold Spring Harbor Press).

Figure 1B:
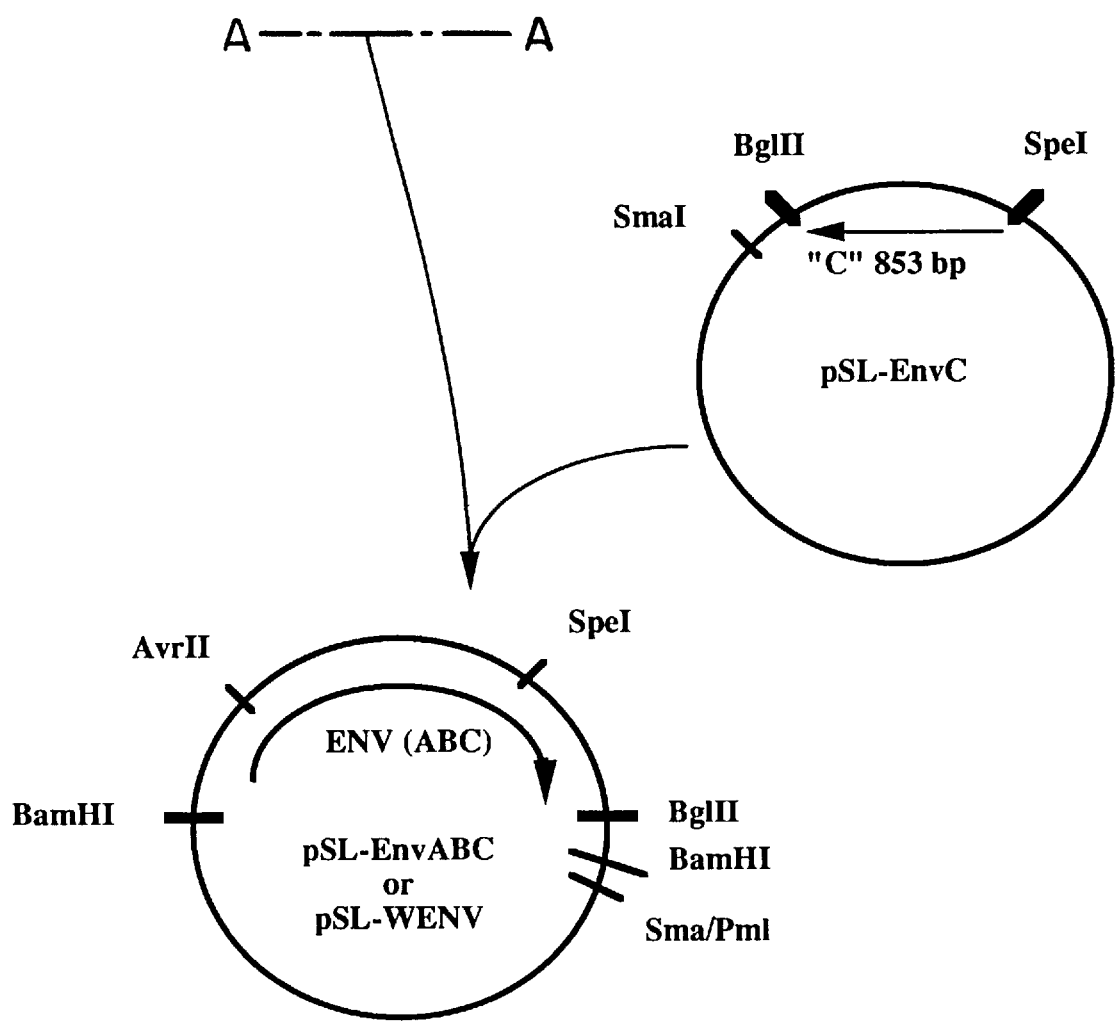

Initially, each fragment was cloned into pSL1190, after which the three fragments were spliced together to re-create a full length envelope gene. For this purpose, the Envelope A plasmid was digested with BamHI and AvrII, the envelope B plasmid was digested was with AvrII and SpeI, and the envelope C plasmid was digested with SpeI and BglII. Subsequently, the 1.5 kbp AvrII/SpeI envelope B fragment was ligated into pSL-EnvA that had been digested with AvrII and SpeI to create pSL-EnvAB (FIG. 1). The envAB fragment codes for the entire surface membrane protein (SU) and the first 63 amino acids from the amino-terminus of the transmembrane protein (TM) of FIV-NCSU-1, i.e., amino acids 1–735 of env. However, envAB does not contain the transmembrane domain (TM).

Figure 2:
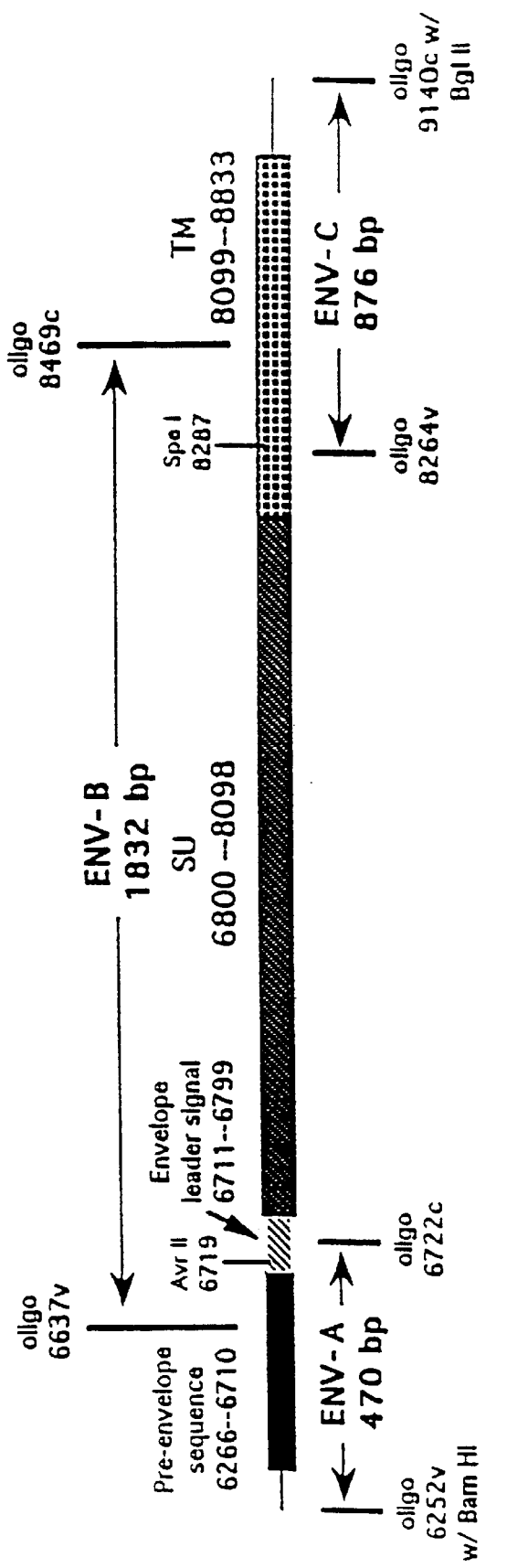
FIG. 2 is a diagrammatic representation of the structure of the recombinant FIV env gene in pSL-EnvABC.

Next, the 0.9 kbp SpeI/SmaI envelope C fragment from pSL-EnvC was ligated into pSL-EnvAB that had been digested with SpeI and BbrPI, to create pSL-EnvABC or pSL-WEnv (FIG. 1). The WEnv fragment codes for the entire env open reading frame (SU and TM proteins) of FIV NCSU-1 (FIG. 2).

The subcloned genetic elements of FIV-NCSU-1 were sequenced using Sequenase Version 2.0 (United States Biochemical, Cleveland, Ohio)) as described for double-stranded DNA, and the reactions were analyzed using the ABI automated sequencer (Applied Biosystems, Foster City, Calif.). Both DNA strands were sequenced to confirm the results. The DNA sequences were analyzed using the MacVector DNA Analysis software (International Biotechnologies, Inc., New Haven, Conn.). The env DNA sequences were analyzed for open reading frames and compared to the previously published DNA sequences of other FIV isolates. The DNA and predicted amino acid sequences of env and envAB open reading frames of FIV-NCSU-1 are shown in FIG. 3.

C. Cloning of The FIV GAG Gene

The gag gene of FIV-NCSU$_1$, was amplified using PCR and the following oligonucleotide primers:

5'-CAATTCTAGAGAGACTCTACAGCAACATG-3' [SEQ. I.D. NO. 7 ](Coding strand, 610-V)

5'-TAATAGATCTGGCCTCTTTTCTAATGATG-3' [SEQ. I.D. NO. 8 ](Complementary strand, 2026-C)

Figure 4:
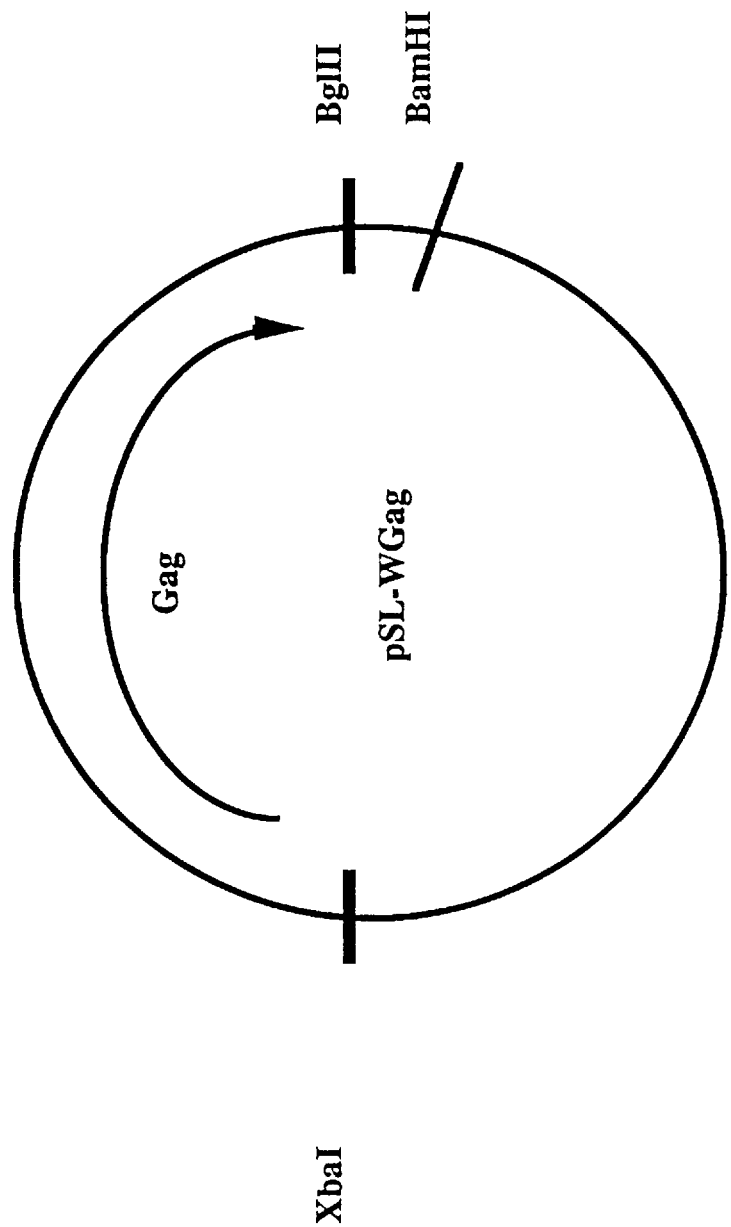
FIG. 4 is a graphic illustration of the pSL-WGag plasmid.
Figure 5F:
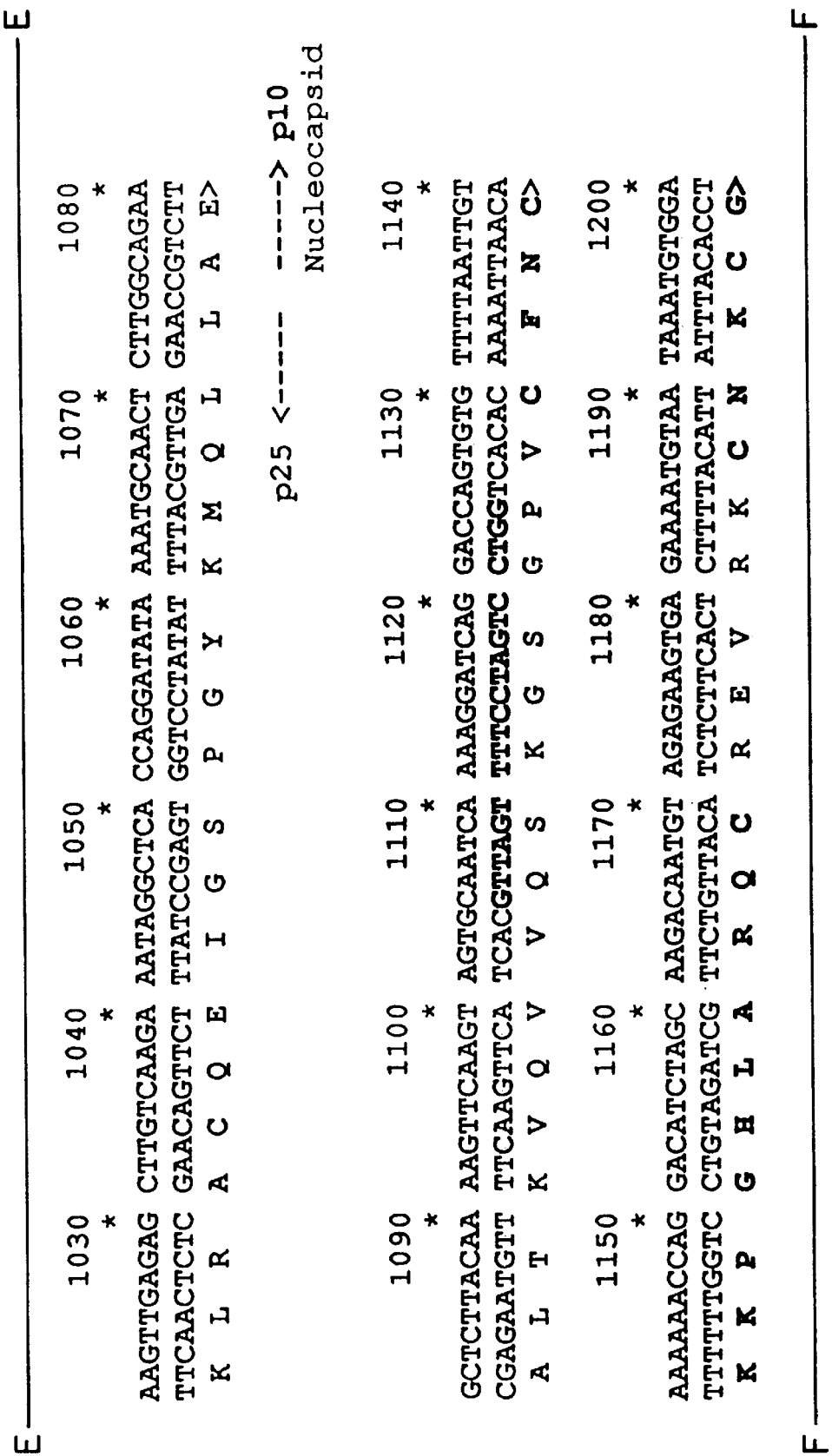
FIGS. 5A–5C show the DNA [SEQ. I.D. NO. 13] and protein [SEQ. I.D. NO. 11] sequence of the gag gene of FIV.
Figure 6:
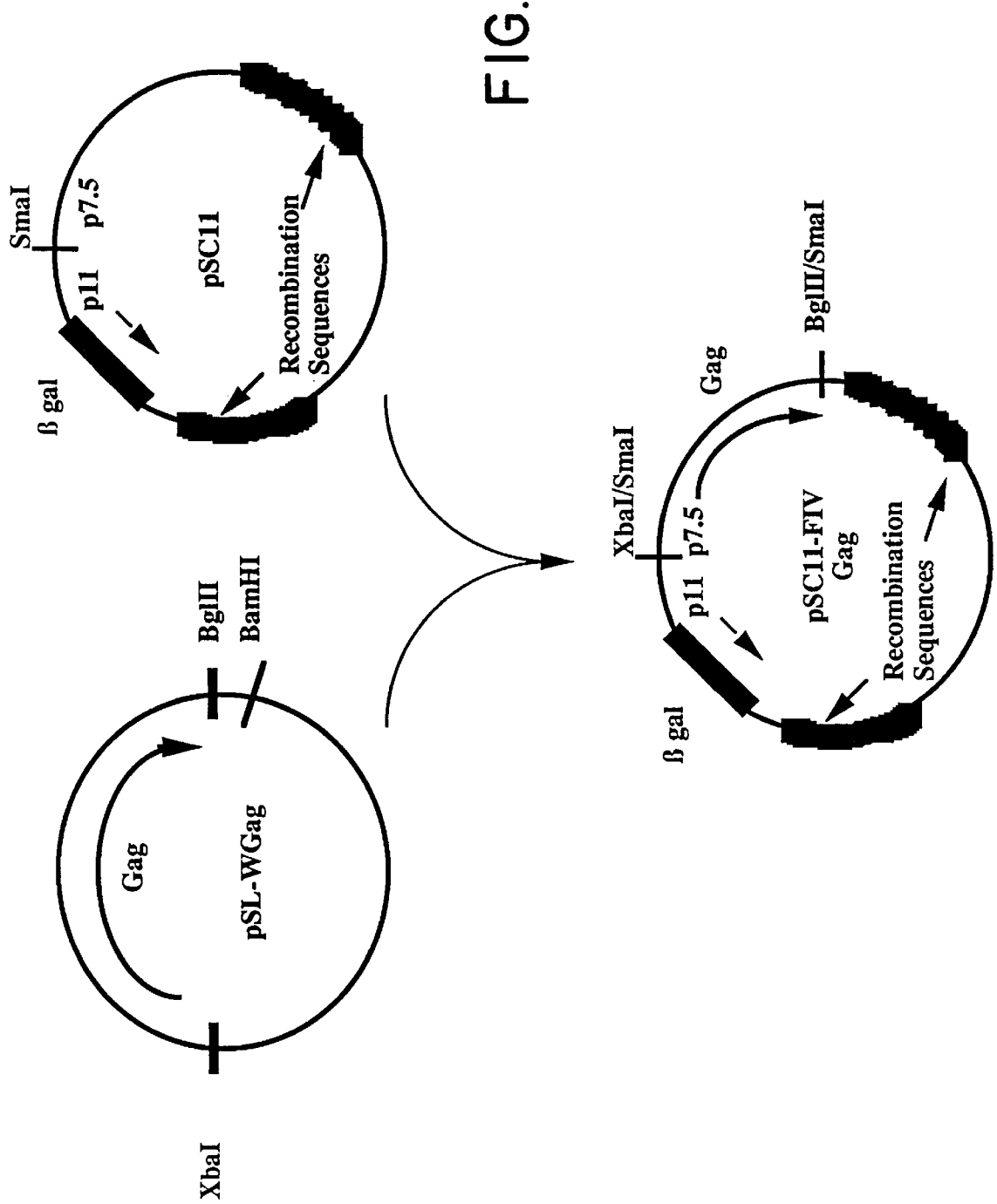
FIG. 6 is a graphic illustration of the cloning strategy for construction of the raccoon poxvirus transfer plasmid pSC11-FIV gag.
Figure 7:
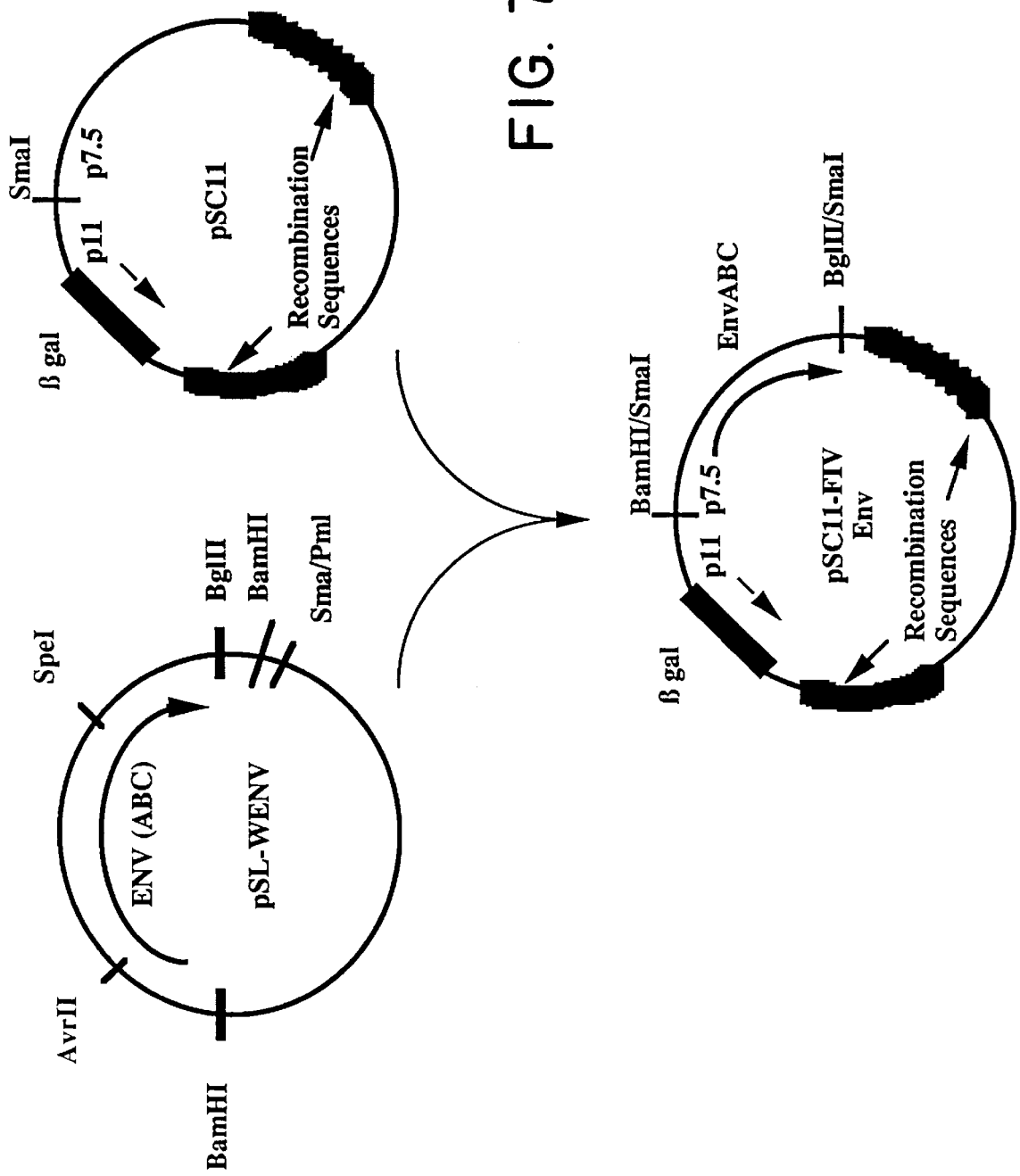
FIG. 7 is a graphic illustration of the cloning strategy for construction of the raccoon poxvirus transfer plasmid pSC11-FIV Env.
Figure 8:
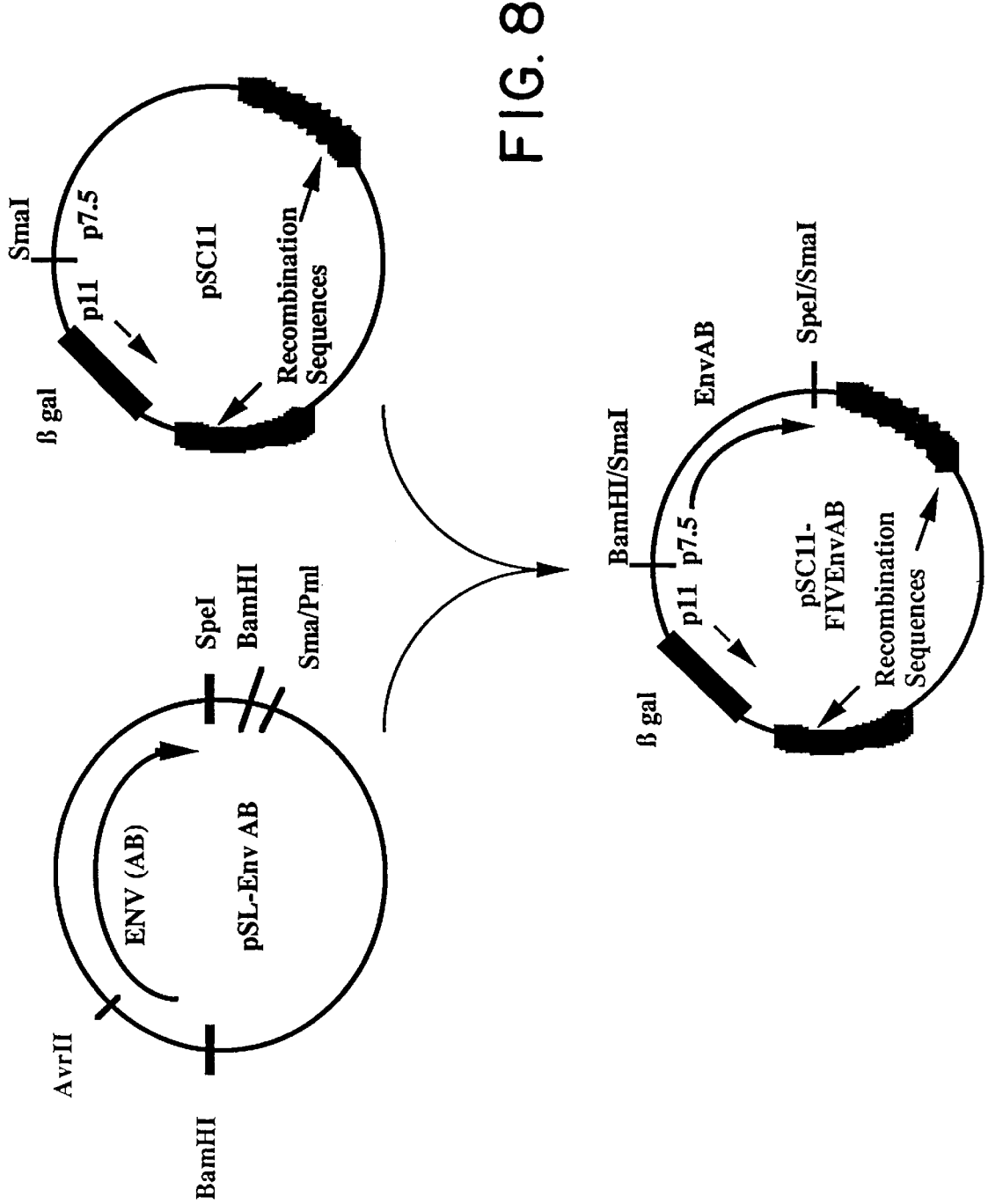
FIG. 8 is a graphic illustration of the cloning strategy for construction of the raccoon poxvirus transfer plasmid pSC 11-FIV EnvAB.

Primers 610-V and 2026-C correspond to nucleotides 610–630 and 2005–2026 of FIV 14 strain, respectively. Primers 610-V and 2026-C have XbaI and BglII restriction enzyme sites, respectively, near their 5' ends to facilitate cloning. The last three nucleotides of primer 610-V correspond to the start codon for gag protein translation. PCR was performed for 35 cycles of 1 min 30 sec at 94° C., 2 min at 56° C., and 2 min at 72° C. followed by one cycle of 4 min at 72° C. The 1.4 kbp DNA fragment containing the gag gene was purified by gel electrophoresis and cloned into the XbaI/BglII site of pSL1190 to form pSL-WGag (FIG. 4). The DNA sequence of FIV-NCSU-1 gag is shown in FIG. 5.

EXAMPLE 2

Preparation of Recombinant Raccoon Poxviruses

A. Construction of Raccoon Poxvirus Transfer Plasmids

The DNA sequences encoding the gag, env, and envAB isolated as described in Example 1 were individually subcloned into the poxvirus transfer vector pSC11. The sequence of pSC11 is disclosed in co-pending U.S. patent application Ser. No. 08/125,516, which is incorporated by reference. For this purpose, the 1.4 kb XbaI/BglII fragment of pSL-WGag (FIG. 6), the 2.9 kb BamH1/SpiI fragment of pSL-WEnv (FIG. 7) and the 2.1 kb BamHI/SpeI fragment of pSL-EnvAB (FIG. 8) were individually isolated and rendered blunt-ended with the Klenow fragment of DNA polymerase, after which each was individually cloned into the Smal site of pSC11.

B. Preparation of Recombinant Raccoon Poxviruses

Recombinant raccoon pox viruses (RRPV) bearing the FIV gag and env genes were prepared as generally described for recombinant vaccinia viruses (Mackett and Smith, *J Gen Virol* 67:2067–2082, 1986) with some modifications. Monolayers of Vero cells (ATCC CCL 81) that were 80% confluent (approximately $5\times10^6$ cells in 100 mm tissue culture dishes) were infected with wild-type raccoon pox virus (ATCC VR-838) at a multiplicity of infection (MOI) of 0.1 $TCID_{50}$/cell in 2 ml of MEM (Eagle's Minimum Essential Medium (Gibco BRL #410–1500) containing 0.05% lactalbumin hydrolysate and 15 $\mu$g/ml gentamicin sulfate, adjusted to pH 7.2 with sodium bicarbonate) for 30–60 minutes at 37° C. The cells were then transfected with either pSC11-FIV gag, pSC11-FIV env, or pSC11-FIV env AB transfer plasmids by cationic liposome-mediated transfection using Transfectam® (Promega Corporation, Madison, Wis.) according to manufacturer's instructions. The cells/DNA-liposomes mixture was incubated in 3 ml of MEM containing 5% fetal bovine serum (FBS) overnight at 37° C. (5% $CO_2$), after which the medium was replaced with 8 ml fresh MEM/5% FBS. The transfected cells were incubated at 37° C. (5% $C0_2$) until greater than 80% of the cells showed cytopathic effects (approximately 3–4 days). The cells and culture media (viral-cell lystates) were then removed from the plates and subject to two cycles of freeze-thawing before storage at −70° C.

C. Isolation of Recombinant Raccoon Pox Virus Carrying the FIV gag Gene

RRPV carrying the FIV-NCSU$_1$gag gene (RRPV-FIV gag) are isolated and purified from the pSC11-FIV gag/Vero cell transfection by standard viral plaque assay methods. Monolayers of Vero cells (50–80% confluent) in 100 mm tissue culture dishes were infected with 2 ml of 10-fold serial dilutions ($10^{-1}$ to $10^{-3}$ in MEM) of the viral-cell lysates. After incubation, for 1 hour at 37° C., the media are removed and the infected cells were overlaid with 8–10 ml of 1.25% Noble agar containing MEM/5% FBS. The infected cells were then incubated for 3–4 days at 37° C. (5% $CO_2$), and overlaid again with 4 ml of 1.25% Nobel agar containing 0.5× PBS and 600 ug/ml 5-bromo-4-chloro-3-indolyl-β-D-galactopyranoside (X-gal, United States Biochemical, Cleveland, Ohio). The plates were incubated at 37° C. (5% $CO_2$) for 4–16 hours, until blue viral plaques (β-galactosidase positive) were observed. The recombinant viral plaques were picked with sterile blunt needles attached to a 1 cc syringe, suspended in 0.5 ml of 0.25 mg/ml trypsin, vortexed vigorously, and incubated at 37° C. for 15–30 minutes. The disrupted viral plaques were then inoculated onto 5×$10^5$ Vero cells in T-25 $cm^2$ flasks and incubated at 37° C. (5% $CO_2$) until greater than 80% CPE was observed. The viral-cell lysates containing RRPV-FIV gag were subjected to two cycles of freeze-thawing and stored at −70° C. Five individual RRPV-FIV gagclones were selected and plaqued purified four times as described above.

D. Isolation of Recombinant Raccoon Pox Virus Carrying FIV envAB Gene

RRPV carrying the FIV-$NCSU_1$ envAB gene (RRPV-FIV envAB) were isolated and purified from the pSC 11-FIV envAB/Vero cell transfection using the methods as described for RRPV-FIV gag with some slight modifications. Thymidine kinase deficient (tk−) raccoon pox viruses from the initial viral-cell lysates were selected on tk−Rat-2 cells (ATCC CRL 1764) This was performed by inoculating 1 ml of the initial viral-cell lysate onto a monolayer of Rat-2 cells in a T-75 $cm^2$ flask (approximately 5×$10^6$ cells) containing 5-bromodeoxyuridine (BrdU) at 30 ug/ml in MEM. The infected monolayer was incubated at 37° C. (5% $CO_2$) for 3–4 days until greater than 70% CPE was observed. The tk− viral-cell lysates were subjected to two cycles of freeze-thawing two times and stored at −70° C. RRPV-FIV envAB were isolated and purified from the tk− viral-cell lysates by the standard viral plaque assay as described above for RRPV-FIV gag on Vero cells. Five individual RRPV-FIV env AB clones were selected and plaque purified five times.

EXAMPLE 3

Characteristics of Recombinant FIV-Expressing Raccoon Pox Viruses

A. Confirmation of FIV gab and envAB Genes in RRPV by Polymerase Chain Reaction

The presence of the FIV gag and envAB genes in the RRPVs was confirmed using PCR. 90 μl of a viral-cell lysate was incubated with 10 μl of 10× PCR lysis buffer (1×; 10 mM Tris-HCl buffer, pH 8.5, containing 50 mM KCl, 2.5 mM $MgCl_2$, 0.5% Tween 20, 0.3 mg/ml Proteinase K) for 16 hours at 50° C., then boiled for 10 minutes. 10 μl of this lysate was used as a template in the PCR reaction. PCR was performed in 100 μl of 10 mM Tris-HCl buffer, pH 8.3, containing 50 mM KCl, 200 uM of each dNTP, 1.5 mM $MgCl_2$, 30 pmoles of each primer, and 2.5 Units of AmpliTaq® DNA polymerase (Perkin-Elmer Cetus, Norwalk, Conn.). The primers used in the PCR for FIV gag were:

5'-TATGGAAAAGGCAAGAGAAGGAC-3' [SEQ. I.D. NO. 9]

5'-TCGAGATACCATGCTCTACACTG-3', [SEQ. I.D. NO. 10]

corresponding to nucleotides 471–493 and 763–785 of the FIV gag open reading frame, respectively. The primers used in the PCR for FIV envAB were:

5'-TATGGAAAAGATGGGATGAGACTA-3'

5'-GTCACTTACCTTCATAGTAAACC-3' corresponding to nucleotides 857–880 and 1513–1535 of the FIV env open reading frame, respectively. The PCR amplifications were performed in a DNA Thermal Cycler (Perkin-Elmer Cetus) by first heating the reaction mixes to 94° C. for denaturation, and then 35 cycles of 1 minute at 95° C., 1 minute at 55° C. , and 2 minutes at 72° C., and a final incubation of 8 minutes at 72° C. 10 μl of the PCR products were analyzed by electrophoresis in a horizontal-submarine 4% NuSieve® agarose (FMC BioProducts, Rockland, Me.) gel in TAE buffer (40 mM Tris base, 20 mM sodium acetate, 1 mM EDTA, pH 7.2) by applying 5 V/cm for 1–2 hours, and staining with ethidium bromide. PCR amplifications with the FIV gag and env primers gave expected DNA fragments of 314 and 678 nucleotides, respectively. PCR amplifications using the pSC11 FIV gag and envAB transfer plasmids served as positive controls. PCR amplifications using wild-type raccoon pox virus-Vero cell lysates served as a negative control.

B. Confirmation of RRPV FIV gag and envAB Protein Expression by Western Blot Analysis Confluent monolayers of Vero cells in a T-25 $cm^2$ flask (1–2×$10^6$ cells) were infected with clones of either RRPV-FIV gag or RRPV-FIV envAB at an M.O.I. of 1 to 10 $TCID_{50}$ per cell. The infected cells were incubated at 37° C. (5% $CO_2$) for 2–3 days until approximately 80% CPE was observed. 20 μl of the viral-cell lysate was added to 5 μl of 5× Laemmli sample buffer (0.3M Tris-HCl buffer, pH 6.8, containing 5% SDS, 50% glycerol, 0.4% bromophenol blue, and 3% 2-mercaptoethanol) and heated at 95° C. for 5 minutes. The denatured protein samples were separated by SDS/polyacrylamide electrophoresis using a 4–15% gradient polyacrylamide gel (Maniatis et al., Molecular Cloning: A Laboratory Manual, 1982, Cold Spring Harbor Press). After electrophoresis, the proteins were transferred to nitrocellulose filters (Bio-Rad Laboratories, Hercules, Calif.) by electrotransfer using a Bio-Rad transfer apparatus per manufacturer's instructions. The transfer was performed in 25 mM Tris-HCl buffer, containing 0.2M glycine and 20% methanol, for 45 minutes at 50V with constant current.

The blot was then screened for FIV gag and envAB proteins by immunoblot analysis as previously described (Davis et al., *Basic Methods in Molecular Biology,* 1986, Elsevier Science Publishing Company, New York, N.Y.) with some slight modifications. After transfer, the nitrocellulose blot was rinsed in phosphate buffer saline, pH 7.4, containing 0.1% Tween-20 (PBS-TW), and non-specific sites were blocked by incubating the blot in PBS containing 1% bovine serum albumin (PBS-BSA) at 4° C. overnight, followed by a 15 minute wash in PBS-TW. The blot was then incubated for 30 minutes at room temperature with goat anti-FIV IgG diluted 1:100 in PBS-TW containing 1% BSA (PBS-TW-BSA), followed by four 5 minute washes in PBS-TW. Next, the blot was incubated for 30 minutes at room temperature with a biotin-labeled mouse-anti-goat IgG antibody (secondary antibody) (Kirkegaard & Perry Laboratories Inc., Gaithersburg, Md.) diluted 1:2000 in PBS-TW-BSA, followed by four 5-minute washes in PBS-TW. Antigen-antibody complexes were detected by, incubating the blot for 30 minutes at room temperature with horseradish peroxidase-conjugated streptavidin (Kirkegaard & Perry Laboratories Inc.) diluted 1:1000 in PBS-TW, washing four times for 5 minutes each in PBS-TW, and visualizing with peroxidase chromogenic substrate (Kirkegaard & Perry Laboratories Inc.). Sucrose-gradient purified FIV and wild-type raccoon pox virus/Vero cell lysates were used as the positive and negative controls for the immunoblot analysis, respectively.

Goat anti-FIV antibodies were prepared as follows. FIV $NCSU_1$ was grown in peripheral blood lymphocytes and concentrated using a hollow fiber apparatus to a concentration of about $10^6$ $TCID_{50}$/ml. The concentrated virus stock was mixed with an oil adjuvant such as OW3 in a ratio of 1:1 (v:v), and the emulsion was used to inoculate goats six times, at intervals of 3–4 weeks. At monthly intervals, the goats were bled and the serum was tested for the presence of anti-FIV antibodies.

C. Confirmation of RRPV FIV gag and envAB Protein Expression by Immunofluorescence Assay Confluent monolayers of Vero cells in 96-well plates ($1–2\times10^4$ cells/well) are infected with clones of either RRPV-FIV gag or RRPV-FIV envAB at a multiplicity of infection of 0.1 to 1.0 plaque forming units per cell. Cell infected with wild-type RCNV serve as a negative control. The infected cells are incubated at 37° C. (5% $CO_2$) for 1 day until approximately 20% CPE is observed. The cells are then washed three times with PBS and fixed with 80% acetone at 4° C. for ten minutes. Next, the cells are rehydrated with PBS and incubated with a monoclonal antibody (IgG) against either FIV gag or env surface membrane proteins for 30 minutes at room temperature. FIV antigen/FIV antibody complexes are detected using a FITC-conjugated goat anti-mouse IgG (Kirkegaard & Perry Laboratories Inc., Gaithersburg, Md.) and fluorescence microscopy.

D. Raccoon Poxvirus Titration

Virus preparations were pre-treated by dilution into an equal volume of 0.5% trypsin and incubation at 37° C. for 30 minutes in order to release virus from inclusions. Serial dilutions (10-fold) of virus were then prepared in MEM and were inoculated (100 $\mu$l/well) in replicates of five onto Vero cells ($1\times10^4$ cells in 100 $\mu$1per well) in a 96 well plate. Plates were incubated for 3–5 days at 37° C. (5% $CO_2$) and observed for cytopathology typical of raccoon poxvirus. Viral infectivity titers were calculated as 50% endpoints based on cytopathology using the methods of Reed and Muench (Reed and Muench, *The American Journal of Hygiene* 27: 493, 1938).

EXAMPLE 4

Preparation of Vaccines Based on Recombinant Pox Viruses

A. Preparation of Master Seeds of RRPV-FIV gag and envAB Viruses

A single clone of each recombinant virus that showed significant recombinant protein expression (by the method described in Example 3 above) was selected for large-scale expansion to serve as a master seed virus. All recombinant virus expansions and titrations were done on Vero cells in MEM containing 2.5% FBS. Each plaque-purified virus clone was expanded by inoculating a confluent monolayer of Vero cells in a T-150 $cm^2$ flask ($1\times10^7$ cells) with 1 ml of viral-cell lysate (approximately $10^7$ infectious virus particles), and incubating at 37° C. (5% $CO_2$) until 100% CPE was observed (2–3 days). This viral-cell lysate served as a pre-master seed virus stock and was used to obtain the master seed virus. The pre-master seed of each recombinant virus was titrated on Vero cells and a $TCID_{50}$ was determined. The master seed viruses for RRPV-FIV gag and RRPV-FIV envAB were grown on Vero cells using an MOI of 0.01 and 0.1, respectively. Three roller bottles of confluent Vero cells were infected for each of the master seed viruses using MEM media supplemented with 2.5% fetal bovine serum and incubated for approximately 3 days at 37° C. Infected culture supernatant fluids were harvested, and seed viruses were aliquoted into 1.5 ml ampules, which were sealed and stored in a liquid nitrogen freezer.

B. Preparation of Vaccines

Vero cells ($3\times10^7$) were seeded into 850 $cm^2$ roller bottles in 200 ml of growth media (MEM containing 0.5% lactalbumin hydrolysate and 5% heat-inactivated fetal bovine serum) and incubated for 18 hours at 37° C. The next day, the media were removed from the cells and replaced with 50 ml of RRPV-FIV gag at a multiplicity of infection of 0.01 in infection media (MEM containing 0.5% LAH and 2.5% heat-inactivated fetal bovine serum). The virus used was at the fourth passage beyond the master seed preparation. Virus was allowed to adsorb to the cells for 30 minutes at 37° C., after which the volume of medium was adjusted to 150 ml per roller bottle. Roller bottles were incubated at 37° C. until 100% cytopathology was evident (3 days). A virus/cell lysate was then prepared and stored frozen (−70° C.). The virus titer of RRPV-FIV gag was determined to be $10^{7.4}$ $TCID_{50}$/ml.

Recombinant raccoon poxviruses expressing the FIV envAB gene fragment were prepared in the same manner, except that a multiplicity of infection of 0.1 was used. The virus was at the fourth passage beyond the master seed preparation. The RRPV-FIV envAB preparation was titered and found to contain $10^{6.4}$ $TCID_{50}$/ml.

Wild type raccoon poxvirus was grown using the same methods as described above. This virus preparation was found to contain $10^{7.7}$ $TCID_{50}$/ml.

EXAMPLE 5

Test of Efficacy of FIV Vaccines Based on Recombinant Pox Viruses

A. Vaccination

Thirty 6–7 month old cats (specific pathogen-free, Harlan Sprague Dawley, Madison, Wis.), fifteen males and fifteen females, were used. Cats were divided into six groups and vaccinated twice, 21 days apart, as indicated below:

TABLE 1

Assignment of Groups for Vaccination

| Group | # Cats | Vaccine | Volume | Virus Dose($TCID_{50}$) | Route* |
|---|---|---|---|---|---|
| 1 | 5 | RRPV-FIV gag | 1 mL | $10^{7.4}$ | SC |
| 2 | 5 | RRPV-FIV gag | 1 mL | $10^{7.4}$ | IM |
| 3 | 5 | RRPV-FIV envAB | 3 mL | $10^{6.9}$ | SC |
| 4 | 5 | RRPV-FIV envAB | 2 mL | $10^{6.7}$ | IM |
| 5 | 5 | RRPV-FIV gag(1 ml) + | 4 mL | $10^{7.4}$ (gag) | SC |
| | | RRPV-FIV envAB | 3 mL | $10^{6.9}$ (envAB) | SC |
| 6 | 5 | Wild Type raccoon pox virus | 1 mL | $10^{7.7}$ | SC |

*SC = Subcutaneous Vaccination
IM = Intramuscular Vaccination

B. Experimental Design

Twenty-five cats were vaccinated with the recombinant raccoon poxvirus vaccines as indicated in Table 1. Five cats were administered a similar titer of wild type raccoon poxvirus to serve a negative controls. Two vaccinations were administered 21 days apart. Subcutaneous vaccinations were administered in the nape of the neck, and intramuscular vaccinations were administered in a rear thigh. Four weeks following the second vaccination, all cats were challenged with the NCSU-1 strain of FIV and monitored for viremia and evidence of lymphocyte population changes as described below. Eleven months following FIV challenge, cats in Groups 1, 2, 3, 4, and 6 were challenged with *Toxoplasma gondii* and monitored for 48 days for clinical signs of disease.

C. FIV Challenge

Four weeks following the second vaccination, all of the cats were challenged subcutaneously with 10 cat $ID_{50}$ units of the $NCSU_1$ isolate of FIV(1:1000 dilution of lot #021891). Whole blood was obtained from the cats prior to challenge, and periodically after challenge, in order to assess virus infection parameters as follows:

1. Detection of Viremia

Culture isolation of FIV was performed as described previously (Wasmoen et al., *Vet. Immuno. Immunopath.* 35:83 1992). Mononuclear cells were isolated from whole blood using Percoll™ (Pharmacia Biotech, Piscataway N.J.) gradients. $5 \times 10^5$ cells from FIV-challenged cats were cultured with $1 \times 10^6$ mononuclear cells isolated from uninfected cats. Cultures were fed with RPMI media every 7 days and supernatants tested for the presence of FIV by an enzyme-linked immunosorbent assay (ELISA) that detects FIV p25 antigen (Petcheck ELISA, IDEXX, Portland Me.).

2. Lymphocyte Subsets

Leukocytes were isolated from whole blood using Histo-paque™ (Sigma Chemical Company, St. Louis Mo.) and lymphocyte subsets quantitated by staining the cells with antibodies specific to CD4 (monoclonal antibody CAT30A), CD8 (monoclonal antibody FLSM 3.357), pan T lymphocytes (monoclonal antibody FLSM 1.572) or B lymphocytes (anti-cat IgG) followed by FACS analysis. These monoclonal antibodies are described elsewhere (Tompkins et al. *Vet. Immunol. Immunopathol.* 26:305, 1990) and the flow cytometry procedure is the same as previously described (R. V. English et al. *J. Infect. Dis.* 170:543, 1994). CD4:CD8 ratios were calculated.

D. Toxoplasma gondii Challenge

Tacheozoites of the ME49 strain of *T. gondii* that were frozen in 10% glycerol were inoculated intraperitoneally into Swiss mice (Charles Rivers Laboratories) and serially passed in mice according to published procedures (Davidson et al., *Am. J. Pathol.* 143:1486, 1993). Tacheozoites harvested from peritoneal fluids of mice were enumerated using a hemacytometer. Cats were tranquilized using ketamine hydrochloride and inoculated with 50,000 fresh tachyzoites into the right common carotid artery that had been surgically isolated. Cats were monitored for clinical signs of disease, including ocular discharge, nasal discharge, dyspnea, fever, depression, and weight loss for 3 days prior to and 48 days following *T. gondii* inoculation.

Clinical signs follow *T. gondii* challenge were scored as follows:

| Clinical Sign | Score |
| --- | --- |
| Fever | |
| 103.0 to 103.9° F. | 1 point per day |
| 104.0 to 104.9° F. | 2 points per day |
| ≧105.0° F. | 3 points per day |
| (Temperatures were not scored until ≧1° F. above baseline.) | |
| Depression/Lethargy | 1 point per day |
| Dehydration | 2 points per day |
| Nasal Discharge | 1 point per day |
| Ocular Discharge | 1 point per day |
| Respiratory Distress: | |
| Tachypnea | 2 points per day |
| Dyspnea | 4 points per day |

E. RESULTS

At one month following inoculation with the NCSU-1 strain of FIV, 60% of the control cats were found to be viremic (FIG. 9). Cats vaccinated with RRPV-FIV gag were all negative for FIV, 40% of the cats vaccinated with RRPV-FIV envAB were virus positive, and 20% of the cats vaccinated with a combination of these two viruses were viremic (FIG. 9). Therefore, the ability of the test vaccines to prevent viremia at this time point varied from 33% to 100% (FIG. 10).

At three months after FIV challenge, 80% of the control cats were found to be virus positive (FIG. 9). Similarly, FIV could be isolated from peripheral blood mononuclear cells of nearly all vaccinated cats using this very sensitive method (FIG. 9).

With respect to immune status, 80% of the control cats showed evidence of CD4:CD8 lymphocyte ratio inversions (i.e. ratios less than 1.0) at three months (FIG. 9). In contrast, only 30% of the RRPV-gag vaccinated cats had evidence of significant CD4:CD8 inversions, and the RRPV-FIV envAB vaccinates were similarly protected from this lymphocyte subset change (FIG. 9). Cats vaccinated with a combination of the two recombinant viruses were not significantly different from the controls (i.e. 80% showed CD4:CD8 inversions) at 3 months after challenge (FIG. 9).

At 9 months after FIV challenge, 100% of the control cats were FIV infected, and all showed CD4:CD8 inversions (FIG. 9). A large percentage of the vaccinated cats were also shown to be viremic at this time point. However, only 50% of the RRPV-FIV gag vaccinates and 20% of the RRPV-FIV envAB vaccinates showed evidence of CD4:CD8 inversions at this time point. Therefore, these two vaccines showed a significant ability to prevent the CD4:CD8 lymphocyte ratio changes associated with FIV infection even though the cats appeared to be viremic (FIG. 10).

In order to determine whether CD4:CD8 lymphocyte subset inversions signified a deterioration in the immune system of cats following FIV infection (and, conversely, that lack of inversion in vaccinates signified maintenance of immune function), vaccinated and control cats (from groups 1, 2, 3, 4, and 6) were challenged with *Toxoplasma gondii*. This parasite causes subclinical infections in normal cats, but has been reported to cause severe disease in cats that are immunocompromised due to FIV infection (Davidson et al., *Am. J. Pathol.* 143:1486, 1993). Following *T. gondii* challenge, control cats displayed ocular discharge, nasal discharge, dyspnea, and fever. The average total clinical score for control cats was 15.6 (FIG. 11). By comparison, there was a 41% reduction in clinical disease scores in RRPV-FIV gag vaccinated cats, related to reductions in clinical signs of ocular discharge and dyspnea (FIG. 11). The clinical picture following *T. gondii* challenge was even less severe in RRPV-FIV envAB vaccinated cats. This group showed a 92% decrease in ocular signs, 75% decrease in nasal discharge, 73% reduction in dyspnea, and 58% decrease in overall clinical scores (FIG. 11). Further, 80% of the control cats displayed weight loss in the first 14 days after challenge, compared to weight loss in only 44% of the RRPV-FIV gag vaccinates and 50% of the V-FIV envAB vaccinates. Therefore, control cats were more susceptible to induction of disease by this opportunistic pathogen than vaccinated cats.

These data suggest that vaccination altered the progression of clinical disease caused by this virus (i.e. induction of immune suppression). This is indicated by a lower rate of CD4:CD8 inversions in vaccinated cats and by a decreased susceptibility to infection with the opportunistic pathogen *T. gondii*.

What is claimed is:

1. A recombinant raccoon poxvirus having at least one internal gene comprising a DNA sequence encoding the envelope protein of Feline Immunodeficiency Virus (FIV) or immunogenic fragments therefrom.

2. The recombinant raccoon poxvirus of claim 1 wherein said internal gene encodes the FIV envelope protein having the amino acid sequence as set out in FIG. 3 or immunogenic fragments therefrom.

3. The recombinant raccoon poxvirus of claim 2 wherein said internal gene encodes amino acids 1–735 of the FIV envelope protein.

4. A vaccine for use in cats comprising:

a recombinant raccoon poxvirus having at least one internal gene comprising a DNA sequence encoding envelope protein of Feline Immunodeficiency Virus (FIV) or immunogenic fragments therefrom, and a pharmaceutically acceptable carrier or diluent.

5. The vaccine of claim 4 further comprising a pharmaceutically acceptable adjuvant.

6. The vaccine of claim 4 wherein said internal gene encodes the FIV envelope protein having the amino acid sequence as set out in FIG. 3 or immunogenic fragments therefrom.

7. The vaccine of claim 4 wherein said internal gene encodes amino acids 1–735 of the FIV envelope protein.

8. The vaccine of claim 4 further comprising immunogens derived from viruses selected from the group consisting of feline leukemia virus, feline panleucopenia virus, feline rhinotracheitis virus, feline calicivirus, feline infectious peritonitis virus, feline herpesvirus, feline enteric coronavirus, and mixtures thereof.

9. The vaccine of claim 4 further comprising inactivated or attenuated feline *Chlamydia psittaci, Microsporum canis*, or mixtures thereof.

10. A recombinant raccoon poxvirus having at least one internal gene comprising a DNA sequence encoding the gag protein of Feline Immunodeficiency Virus (FIV) or immunogenic fragments therefrom;

said recombinant raccoon pox virus having the property of preventing a CD4:CD8 lymphocyte radio change associate with FIV infection.

11. The recombinant raccoon poxvirus of claim 10 wherein said internal gene encodes the FIV envelope protein having the amino acid sequence as set out in FIG. 3 or immunogenic fragments therefrom.

12. The recombinant raccoon poxvirus of claim 11 wherein said internal gene encodes amino acids 1–735 of the FIV envelope protein.

13. A vaccine for use in cats comprising:

a recombinant raccoon poxvirus having at least one internal gene comprising a DNA sequence encoding envelope protein of Feline Immunodeficiency Virus (FIV) or immunogenic fragments therefrom, and a pharmaceutically acceptable carrier or diluent;

said vaccine having the property of preventing a CD4:CD8 lymphocyte ratio change associated with FIV infection.

14. The vaccine of claim 13 further comprising a pharmaceutically acceptable adjuvant.

15. The vaccine of claim 13 wherein said internal gene encodes the FIV envelope protein having the amino acid sequence as set out in FIG. 3 or immunogenic fragments therefrom.

16. The vaccine of claim 13 wherein said internal gene encodes amino acids 1–735 of the FIV envelope protein.

17. The vaccine of claim 13 further comprising immunogens derived from viruses selected from the group consisting of feline leukemia virus, feline panleucopenia virus, feline rhinotracheitis virus, feline calicivirus, feline infectious peritonitis virus, feline herpesvirus, feline enteric coronavirus, and mixtures thereof.

18. The vaccine of claim 13 further comprising inactivated or attenuated feline *Chlamydia psittaci, Microsporum canis*, or mixtures thereof.

19. A recombinant raccoon poxvirus having at least one internal gene comprising a DNA sequence encoding the envelope protein of Feline Immunodeficiency Virus (FIV).

20. A vaccine for use in cats comprising:

a recombinant raccoon poxvirus having at least one internal gene comprising a DNA sequence encoding envelope protein of Feline Immunodeficiency Virus (FIV), and a pharmaceutically acceptable carrier or diluent.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( B ) STRAIN: 14

( v i i i ) POSITION IN GENOME:
        ( B ) MAP POSITION: 6637-6659
        ( C ) UNITS: bp ( x i ) SEQUENCE DESCRIPTION: SEQ ID NO:1:

TATAGAAGCA CCCCAAGAAG AG      22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( v i ) ORIGINAL SOURCE:
        ( A ) ORGANISM: feline immunodeficiency virus
        ( B ) STRAIN: 14

( x i ) SEQUENCE DESCRIPTION: SEQ ID NO:2:

CATTCCCCCA AAGTTATATT TC      22

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( B ) STRAIN: 14

( v i i i ) POSITION IN GENOME:
        ( B ) MAP POSITION: 8264-8285
        ( C ) UNITS: bp ( x i ) SEQUENCE DESCRIPTION: SEQ ID NO:3:

TTAGTTACAT TAGAGCATCA AG                                            2 2

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( v i ) ORIGINAL SOURCE:
        ( A ) ORGANISM: feline immunodeficiency virus
        ( B ) STRAIN: PPR ( v i i i ) POSITION IN GENOME:
        ( B ) MAP POSITION: 9126-9145
        ( C ) UNITS: bp ( x i ) SEQUENCE DESCRIPTION: SEQ ID NO:4:

TTCTAGATCT TCAGGGTCCC AATACTC                                       2 7

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( B ) STRAIN: 14

( v i i i ) POSITION IN GENOME:
        ( B ) MAP POSITION: 610-630
        ( C ) UNITS: bp ( x i ) SEQUENCE DESCRIPTION: SEQ ID NO:5:

CAATTCTAGA GAGACTCTAC AGCAACATG                                     2 9

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( B ) STRAIN: 14

( v i i i ) POSITION IN GENOME:
        ( B ) MAP POSITION: 2005-2026
        ( C ) UNITS: bp ( x i ) SEQUENCE DESCRIPTION: SEQ ID NO:6:

TAATAGATCT GGCCTCTTTT CTAATGATG                                     2 9

( 2 ) INFORMATION FOR SEQ ID NO:7:

( i ) SEQUENCE CHARACTERISTICS:

(A) LENGTH: 23 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: feline immunodeficiency virus
(C) INDIVIDUAL ISOLATE: NCSU-1

(viii) POSITION IN GENOME:
(B) MAP POSITION: 471-493
(C) UNITS: bp (xi) SEQUENCE DESCRIPTION: SEQ ID NO:7:

TATGGAAAAG GCAAGAGAAG GAC 23

(2) INFORMATION FOR SEQ ID NO:8:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: feline immunodeficiency virus
(C) INDIVIDUAL ISOLATE: NCSU-1

(viii) POSITION IN GENOME:
(B) MAP POSITION: 763-785
(C) UNITS: bp (xi) SEQUENCE DESCRIPTION: SEQ ID NO:8:

TCGAGATACC ATGCTCTACA CTG 23

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: feline immunodeficiency virus
(C) INDIVIDUAL ISOLATE: NCSU-1

(viii) POSITION IN GENOME:
(B) MAP POSITION: 857-880
(C) UNITS: bp (xi) SEQUENCE DESCRIPTION: SEQ ID NO:9:

TATGGAAAAG ATGGGATGAG ACTA 24

(2) INFORMATION FOR SEQ ID NO:10:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: feline immunodeficiency virus
(C) INDIVIDUAL ISOLATE: NCSU-1

(v i i i) POSITION IN GENOME:
  (B) MAP POSITION: 1513-1535
  (C) UNITS: bp (x i) SEQUENCE DESCRIPTION: SEQ ID NO:10:

GTCACTTACC TTCATAGTAA ACC                23

(2) INFORMATION FOR SEQ ID NO:11:

(i) SEQUENCE CHARACTERISTICS:
    (A) LENGTH: 449 amino acids
    (B) TYPE: amino acid
    (C) STRANDEDNESS: single
    (D) TOPOLOGY: linear (i i) MOLECULE TYPE: protein (v i) ORIGINAL SOURCE:
    (A) ORGANISM: feline immunodeficiency virus
    (C) INDIVIDUAL ISOLATE: NCSU-1

(x i) SEQUENCE DESCRIPTION: SEQ ID NO:11:

```
Met Gly Asn Gly Gln Gly Arg Asp Trp Lys Met Ala Ile Lys Arg Cys
1               5                   10                  15

Ser Asn Ala Ala Val Gly Val Gly Gly Lys Ser Lys Lys Phe Gly Glu
            20              25                  30

Gly Asn Phe Arg Trp Ala Ile Arg Met Ala Asn Val Ser Thr Gly Arg
        35                  40                  45

Glu Pro Gly Asp Ile Pro Glu Thr Leu Asp Gln Leu Arg Leu Val Ile
    50                  55                  60

Cys Asp Leu Gln Glu Arg Arg Lys Lys Phe Gly Ser Cys Lys Glu Ile
65                  70                  75                  80

Asp Lys Ala Ile Val Thr Leu Lys Val Phe Ala Ala Val Gly Leu Leu
                85                  90                  95

Asn Met Thr Val Ser Ser Ala Ala Ala Glu Asn Met Phe Thr Gln
                100                 105                 110

Met Gly Leu Asp Thr Arg Pro Ser Met Lys Glu Ala Gly Gly Lys Glu
            115                 120                 125

Glu Gly Pro Pro Gln Ala Phe Pro Ile Gln Thr Val Asn Gly Val Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Pro Thr Asp Met Ala Thr Leu Ile Met Ala
                180                 185                 190

Ala Pro Gly Cys Ala Ala Asp Lys Glu Ile Leu Asp Glu Ser Leu Lys
            195                 200                 205

Gln Leu Thr Ala Gly Tyr Asp Arg Thr His Pro Pro Asp Ala Pro Arg
    210                 215                 220

Pro Leu Pro Tyr Phe Thr Ala Ala Glu Ile Met Gly Ile Gly Phe Thr
225                 230                 235                 240

Gln Glu Gln Gln Ala Glu Ala Arg Phe Ala Pro Ala Arg Met Gln Cys
                245                 250                 255

Arg Ala Trp Tyr Leu Glu Gly Leu Gly Lys Leu Gly Ala Ile Lys Ala
            260                 265                 270

Lys Ser Pro Arg Ala Val Gln Leu Arg Gln Gly Ala Lys Glu Asp Tyr
            275                 280                 285

Ser Ser Phe Ile Asp Arg Leu Phe Ala Gln Ile Asp Gln Glu Gln Asn
```

-continued

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Thr 305 | Ala | Glu | Val | Lys | Leu 310 | Tyr | Leu | Lys | Gln | Ser 315 | Leu | Ser | Met | Ala | Asn 320 |
| Ala | Asn | Ala | Glu | Cys 325 | Lys | Lys | Pro | Met | Thr 330 | His | Leu | Lys | Pro | Glu 335 | Ser |
| Thr | Leu | Glu | Glu 340 | Lys | Leu | Arg | Ala | Cys 345 | Gln | Glu | Ile | Gly | Ser 350 | Pro | Gly |
| Tyr | Lys | Met 355 | Gln | Leu | Leu | Ala | Glu 360 | Ala | Leu | Thr | Lys | Val 365 | Gln | Val | Val |
| Gln | Ser | Lys 370 | Gly | Ser | Gly | Pro 375 | Val | Cys | Phe | Asn | Cys 380 | Lys | Lys | Pro | Gly |
| His 385 | Leu | Ala | Arg | Gln | Cys 390 | Arg | Glu | Val | Arg | Lys 395 | Cys | Asn | Lys | Cys | Gly 400 |
| Lys | Pro | Gly | His | Val 405 | Ala | Ala | Lys | Cys | Trp 410 | Gln | Gly | Asn | Arg | Lys 415 | Asn |
| Ser | Gly | Asn | Trp 420 | Lys | Ala | Gly | Arg | Ala 425 | Ala | Ala | Pro | Val | Asn 430 | Gln | Val |
| Gln | Gln | Ala 435 | Val | Met | Pro | Ser | Pro 440 | Pro | Met | Glu | Glu | Lys 445 | Leu | Leu | Asp |
| Leu |

(2) INFORMATION FOR SEQ ID NO:12:

(i) SEQUENCE CHARACTERISTICS:
(A) LENGTH: 855 amino acids
(B) TYPE: amino acid
(C) STRANDEDNESS: single
(D) TOPOLOGY: linear (ii) MOLECULE TYPE: protein (vi) ORIGINAL SOURCE:
(A) ORGANISM: feline immunodeficiency virus
(C) INDIVIDUAL ISOLATE: NCSU-1

(xi) SEQUENCE DESCRIPTION: SEQ ID NO:12:

| Met 1 | Ala | Glu | Gly | Phe 5 | Ala | Ala | Asn | Arg | Gln 10 | Trp | Ile | Gly | Glu | Glu 15 | Ala |
| Glu | Glu | Leu | Leu 20 | Asp | Phe | Asp | Ile | Ala 25 | Thr | Gln | Met | Asn | Glu 30 | Glu | Gly |
| Pro | Leu | Asn 35 | Pro | Gly | Met | Asn | Pro 40 | Phe | Arg | Val | Pro | Gly 45 | Ile | Thr | Asp |
| Lys | Glu 50 | Lys | Gln | Asp | Tyr | Cys 55 | Asn | Ile | Leu | Gln | Pro 60 | Lys | Leu | Gln | Asp |
| Leu 65 | Arg | Asn | Glu | Leu | Gln 70 | Glu | Val | Lys | Leu | Glu 75 | Glu | Gly | Asn | Ala | Gly 80 |
| Lys | Phe | Arg | Arg | Thr 85 | Arg | Phe | Leu | Arg | Tyr 90 | Ser | Asp | Glu | Gln | Val 95 | Leu |
| Ser | Pro | Val | His 100 | Ala | Phe | Ile | Gly | Tyr 105 | Cys | Ile | Tyr | Leu | Gly 110 | Asn | Arg |
| Asn | Lys | Leu 115 | Gly | Ser | Leu | Arg | His 120 | Ile | Asp | Ile | Glu | Ala 125 | Pro | Pro |
| Glu | Glu | Cys 130 | Tyr | Asp | Asn | Arg | Glu 135 | Lys | Gly | Thr | Thr | Asp 140 | Asn | Ile | Lys |
| Tyr | Gly 145 | Arg | Arg | Cys | Cys 150 | Leu | Gly | Thr | Val | Thr 155 | Leu | Tyr | Leu | Ile | Leu 160 |
| Phe | Ile | Gly | Leu | Ile 165 | Ile | Tyr | Ser | Gln | Thr 170 | Ala | Asp | Ala | Gln | Val 175 | Val |

```
Trp  Arg  Leu  Pro  Pro  Leu  Val  Val  Pro  Val  Glu  Glu  Ser  Glu  Ile  Ile
              180                      185                      190

Phe  Trp  Asp  Cys  Trp  Ala  Pro  Glu  Glu  Pro  Ala  Cys  Gln  Asp  Phe  Leu
         195                      200                      205

Gly  Ala  Met  Ile  His  Leu  Lys  Ala  Lys  Thr  Asn  Ile  Ser  Ile  Arg  Glu
    210                      215                      220

Gly  Pro  Thr  Leu  Gly  Asn  Trp  Ala  Arg  Glu  Ile  Trp  Ala  Thr  Leu  Phe
225                           230                      235                      240

Lys  Lys  Ala  Thr  Arg  Gln  Cys  Arg  Arg  Gly  Arg  Ile  Trp  Lys  Arg  Trp
                   245                      250                      255

Asp  Glu  Thr  Ile  Thr  Gly  Pro  Ser  Gly  Cys  Ala  Asn  Asn  Thr  Cys  Tyr
              260                      265                      270

Asn  Val  Ser  Ala  Ile  Val  Pro  Asp  Tyr  Gln  Arg  Tyr  Leu  Asp  Arg  Val
         275                      280                      285

Asp  Thr  Trp  Leu  Gln  Gly  Lys  Ile  Asn  Ile  Ser  Leu  Cys  Leu  Thr  Gly
    290                      295                      300

Gly  Lys  Met  Leu  Tyr  Asn  Lys  Val  Thr  Lys  Gln  Leu  Ser  Tyr  Cys  Thr
305                           310                      315                      320

Asp  Pro  Leu  Gln  Ile  Pro  Leu  Ile  Asn  Tyr  Thr  Phe  Gly  Pro  Asn  Gln
                   325                      330                      335

Thr  Cys  Met  Trp  Asn  Thr  Ser  Gln  Ile  Gln  Asp  Pro  Glu  Ile  Pro  Gln
              340                      345                      350

Cys  Gly  Trp  Trp  Asn  His  Met  Ala  Tyr  Tyr  Asn  Ser  Cys  Lys  Trp  Glu
         355                      360                      365

Glu  Ala  Lys  Val  Lys  Phe  His  Cys  Gln  Arg  Thr  Gln  Ser  Gln  Pro  Gly
370                           375                      380

Ser  Trp  Arg  Arg  Ala  Ile  Ser  Ser  Trp  Lys  Gln  Arg  Asn  Arg  Trp  Glu
385                           390                      395                      400

Trp  Arg  Pro  Asp  Phe  Glu  Ser  Glu  Lys  Val  Lys  Ile  Ser  Leu  Gln  Cys
                   405                      410                      415

Asn  Ser  Thr  Lys  Asn  Leu  Thr  Phe  Ala  Met  Arg  Ser  Ser  Gly  Asp  Tyr
              420                      425                      430

Gly  Glu  Val  Thr  Gly  Ala  Trp  Ile  Glu  Phe  Gly  Cys  His  Arg  Asn  Lys
         435                      440                      445

Ser  Asn  Leu  His  Thr  Glu  Ala  Arg  Phe  Arg  Ile  Arg  Cys  Arg  Trp  Asn
    450                      455                      460

Val  Gly  Ser  Asp  Thr  Ser  Leu  Ile  Asp  Thr  Cys  Gly  Asn  Thr  Pro  Asn
465                           470                      475                      480

Val  Ser  Gly  Ala  Asn  Pro  Val  Asp  Cys  Thr  Met  Tyr  Ser  Asn  Lys  Met
                   485                      490                      495

Tyr  Lys  Phe  Ser  Leu  Pro  Asn  Gly  Phe  Thr  Met  Lys  Val  Asp  Asp  Leu
              500                      505                      510

Ile  Met  His  Phe  Asn  Met  Pro  Lys  Ala  Val  Glu  Met  Asn  Asn  Ile  Ala
         515                      520                      525

Gly  Asn  Trp  Ser  Cys  Thr  Ser  Asp  Leu  Pro  Ser  Ser  Trp  Gly  Tyr  Met
    530                      535                      540

Asn  Cys  Asn  Cys  Pro  Asn  Ser  Ser  Ser  Tyr  Ser  Gly  Thr  Lys  Met
545                           550                      555                      560

Ala  Cys  Pro  Ser  Asn  Arg  Gly  Ile  Leu  Arg  Asn  Trp  Tyr  Asn  Pro  Val
                   565                      570                      575

Ala  Gly  Leu  Arg  Gln  Ser  Leu  Glu  Gln  Tyr  Gln  Val  Val  Lys  Gln  Pro
                   580                      585                      590

Asp  Tyr  Leu  Leu  Val  Pro  Glu  Glu  Val  Met  Glu  Tyr  Lys  Pro  Arg  Arg
```

|     |     |     |     |     | 595 |     |     |     |     | 600 |     |     |     |     | 605 |     |     |     |
| --- | --- | --- | --- | --- | --- | --- | --- | --- | --- | --- | --- | --- | --- | --- | --- | --- | --- | --- |
| Lys | Arg | Ala | Ala | Ile | His | Val | Met | Leu | Ala | Leu | Ala | Thr | Val | Leu | Ser |
|     | 610 |     |     |     | 615 |     |     |     |     | 620 |     |     |     |     |     |
| Ile | Ala | Gly | Ala | Gly | Thr | Gly | Ala | Thr | Ala | Ile | Gly | Met | Val | Thr | Gln |
| 625 |     |     |     |     | 630 |     |     |     |     | 635 |     |     |     |     | 640 |
| Tyr | His | Gln | Val | Leu | Ala | Thr | His | Gln | Glu | Ser | Met | Glu | Lys | Val | Thr |
|     |     |     |     | 645 |     |     |     | 650 |     |     |     |     |     | 655 |     |
| Glu | Ala | Leu | Glu | Ile | Asn | Asn | Leu | Arg | Leu | Val | Thr | Leu | Glu | His | Gln |
|     |     |     | 660 |     |     |     |     | 665 |     |     |     |     | 670 |     |     |
| Val | Leu | Val | Ile | Gly | Leu | Lys | Val | Glu | Ala | Met | Glu | Lys | Phe | Leu | Tyr |
|     |     | 675 |     |     |     |     | 680 |     |     |     |     | 685 |     |     |     |
| Thr | Ala | Phe | Ala | Met | Gln | Glu | Leu | Gly | Cys | Asn | Pro | Asn | Gln | Phe | Phe |
|     |     | 690 |     |     |     | 695 |     |     |     |     | 700 |     |     |     |     |
| Ser | Lys | Ile | Pro | Leu | Glu | Leu | Trp | Thr | Arg | Tyr | Asn | Met | Thr | Ile | Asn |
| 705 |     |     |     |     | 710 |     |     |     |     | 715 |     |     |     |     | 720 |
| Gln | Thr | Ile | Trp | Asn | His | Gly | Asn | Ile | Thr | Leu | Gly | Glu | Trp | Tyr | Asn |
|     |     |     |     | 725 |     |     |     |     | 730 |     |     |     |     | 735 |     |
| His | Thr | Lys | Asp | Leu | Gln | Pro | Lys | Phe | Tyr | Glu | Ile | Ile | Met | Asp | Ile |
|     |     |     |     | 740 |     |     |     |     | 745 |     |     |     |     | 750 |     |
| Glu | Pro | Asn | Asn | Val | Gln | Gly | Lys | Thr | Gly | Ile | Gln | Gln | Leu | Pro | Lys |
|     |     |     | 755 |     |     |     |     | 760 |     |     |     |     | 765 |     |     |
| Trp | Glu | Asp | Trp | Val | Arg | Trp | Ile | Gly | Asn | Ile | Pro | Gln | Tyr | Leu | Lys |
|     |     | 770 |     |     |     |     | 775 |     |     |     |     | 780 |     |     |     |
| Gly | Leu | Leu | Gly | Gly | Ile | Leu | Gly | Ile | Gly | Leu | Gly | Val | Leu | Leu | Leu |
| 785 |     |     |     |     |     | 790 |     |     |     |     | 795 |     |     |     | 800 |
| Ile | Leu | Cys | Leu | Pro | Thr | Leu | Val | Asp | Cys | Ile | Arg | Asn | Cys | Ile | His |
|     |     |     |     | 805 |     |     |     |     | 810 |     |     |     |     | 815 |     |
| Lys | Ile | Leu | Gly | Tyr | Thr | Val | Ile | Ala | Met | Pro | Glu | Val | Glu | Gly | Glu |
|     |     |     | 820 |     |     |     |     | 825 |     |     |     |     | 830 |     |     |
| Glu | Ile | Gln | Pro | Gln | Met | Glu | Leu | Arg | Arg | Asn | Gly | Ser | Gln | Phe | Gly |
|     |     |     | 835 |     |     |     |     | 840 |     |     |     |     | 845 |     |     |
| Met | Ser | Glu | Lys | Glu | Glu | Glu |     |     |     |     |     |     |     |     |     |
|     | 850 |     |     |     |     | 855 |     |     |     |     |     |     |     |     |     |

( 2 ) INFORMATION FOR SEQ ID NO:13:

( i ) SEQUENCE CHARACTERISTICS:
        ( A ) LENGTH: 1353 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: feline immunodeficiency virus
        ( C ) INDIVIDUAL ISOLATE: NCSU-1

( v i i i ) POSITION IN GENOME:
        ( B ) MAP POSITION: 1-1353
        ( C ) UNITS: bp ( x i ) SEQUENCE DESCRIPTION: SEQ ID NO:13:

```
ATGGGGAATG  GACAGGGGCG  AGATTGGAAA  ATGGCCATTA  AGAGATGTAG  TAATGCTGCT      60

GTAGGAGTAG  GGGGGAAGAG  TAAAAAATTT  GGGGAAGGGA  ATTTCAGATG  GGCCATTAGA     120

ATGGCTAATG  TATCTACAGG  ACGAGAACCT  GGTGATATAC  CAGAGACTTT  AGATCAACTA     180

AGGTTGGTTA  TTTGCGATTT  ACAAGAAAGA  AGAAAAAAAT  TTGGATCTTG  CAAAGAAATT     240

GATAAGGCAA  TTGTTACATT  AAAAGTCTTT  GCGGCAGTAG  GACTTTTAAA  TATGACAGTG     300
```

```
TCTTCTGCTG CTGCAGCTGA AAATATGTTC ACTCAGATGG GATTAGACAC TAGACCATCT      360
ATGAAAGAAG CAGGAGGAAA AGAGGAAGGC CCTCCACAGG CATTTCCTAT TCAAACAGTA      420
AATGGAGTAC CACAATATGT AGCACTTGAC CCAAAAATGG TGTCCATTTT TATGGAAAAG      480
GCAAGAGAAG GATTAGGAGG TGAGGAAGTT CAGCTATGGT TCACTGCCTT CTCTGCAAAT      540
TTAACACCTA CTGACATGGC CACATTAATA ATGGCCGCAC CAGGGTGCGC TGCAGATAAA      600
GAAATATTGG ATGAAAGCTT AAAGCAACTT ACTGCAGGAT ATGATCGTAC ACATCCCCCT      660
GATGCTCCCA GACCATTACC CTATTTTACT GCAGCAGAAA TTATGGGTAT TGGATTTACT      720
CAAGAACAAC AAGCAGAAGC AAGATTTGCA CCAGCTAGGA TGCAGTGTAG AGCATGGTAT      780
CTCGAGGGAC TAGGAAAATT GGGCGCCATA AAAGCTAAGT CTCCTCGAGC TGTGCAGTTA      840
AGACAAGGAG CTAAGGAAGA TTATTCATCC TTTATTGACA GATTGTTTGC CCAAATAGAT      900
CAAGAACAAA ATACAGCTGA AGTTAAGTTA TATTTAAAAC AGTCATTAAG CATGGCTAAT      960
GCTAATGCAG AATGTAAAAA GCCAATGACC CACCTTAAGC CAGAAAGTAC CCTAGAAGAA     1020
AAGTTGAGAG CTTGTCAAGA AATAGGCTCA CCAGGATATA AAATGCAACT CTTGGCAGAA     1080
GCTCTTACAA AAGTTCAAGT AGTGCAATCA AAAGGATCAG GACCAGTGTG TTTTAATTGT     1140
AAAAAACCAG GACATCTAGC AAGACAATGT AGAGAAGTGA GAAAATGTAA TAAATGTGGA     1200
AAACCTGGTC ATGTAGCTGC CAAATGTTGG CAAGGAAATA GAAAGAATTC GGGAAACTGG     1260
AAGGCGGGGC GAGCTGCAGC CCCAGTGAAT CAAGTGCAGC AAGCAGTAAT GCCATCTGCA     1320
CCTCCAATGG AGGAGAAACT ATTGGATTTA TAA                                   1353

( 2 ) INFORMATION FOR SEQ ID NO:14:

( i ) SEQUENCE CHARACTERISTICS:
                        ( A ) LENGTH: 3225 base pairs
                        ( B ) TYPE: nucleic acid
                        ( C ) STRANDEDNESS: single
                        ( D ) TOPOLOGY: linear ( i i ) MOLECULE TYPE: DNA (genomic)

( v i ) ORIGINAL SOURCE:
                        ( A ) ORGANISM: feline immunodeficiency virus
                        ( C ) INDIVIDUAL ISOLATE: NCSU-1

( v i i i ) POSITION IN GENOME:
                        ( B ) MAP POSITION: 1-3225
                        ( C ) UNITS: bp ( x i ) SEQUENCE DESCRIPTION: SEQ ID NO:14:

GGATCCAACA ATAATTATGG CAGAAGGATT TGCAGCCAAT AGACAATGGA TAGGACCAGA       60
AGAAGCTGAA GAGTTATTAG ATTTTGATAT AGCAACACAA ATGAATGAAG AAGGGCCACT      120
AAATCCAGGG ATGAACCCAT TTAGGGTACC TGGAATAACA GATAAAGAAA AGCAAGACTA      180
TTGTAACATA TTACAACCTA AGTTACAAGA TTTACGGAAT GAACTTCAAG AGGTAAAACT      240
AGAAGAAGGA AATGCAGGTA AGTTTAGAAG AACAAGATTT TAAGGTATT CTGATGAACA      300
AGTATTGTCC CCGGTTCATG CGTTCATAGG ATATTGTATT TATTTAGGTA ATCGAAATAA      360
GTTAGGATCT TTAAGACATG ACATTGATAT TGAAGCACCC CCCGAAGAGT GTTATGATAA      420
TAGAGAGAAG GGTACAACTG ACAATATAAA ATATGGTAGA CGATGTTGCC TAGGAACGGT      480
GACTTTGTAC CTGATTTTAT TTATAGGATT AATAATATAT TCACAGACAG CCGACGCTCA      540
GGTAGTATGG AGACTTCCAC CATTAGTAGT CCCAGTAGAA GAATCAGAAA TAATTTTTTG      600
GGATTGTTGG GCACCAGAAG AACCCGCCTG TCAGGACTTT CTTGGGGCAA TGATACATCT      660
```

```
AAAAGCTAAG  ACAAATATAA  GTATACGAGA  GGGACCTACC  TTGGGGAATT  GGGCTAGAGA   720
AATATGGGCA  ACATTATTCA  AAAAGGCTAC  TAGACAATGT  AGAAGAGGCA  GAATATGGAA   780
AAGATGGGAT  GAGACTATAA  CAGGACCATC  AGGATGTGCT  AATAACACAT  GTTATAATGT   840
TTCAGCAATA  GTACCTGATT  ATCAGCGTTA  TTTAGATAGA  GTAGATACTT  GGTTACAAGG   900
GAAAATAAAT  ATATCATTAT  GTCTAACAGG  AGGAAAAATG  TTGTACAATA  AAGTTACAAA   960
ACAATTAAGC  TATTGTACAG  ACCCATTACA  AATCCCACTG  ATCAATTATA  CATTTGGACC  1020
TAATCAAACA  TGTATGTGGA  ATACTTCACA  AATTCAGGAC  CCTGAAATAC  ACAATGTGG   1080
ATGGTGGAAT  CACATGGCCT  ATTATAACAG  TTGTAAATGG  GAAGAGGCAA  AGGTAAAGTT  1140
TCATTGTCAA  AGAACACAGA  GTCAGCCTGG  GTCATGGCGT  AGAGCAATCT  CGTCATGGAA  1200
ACAAAGAAAT  AGATGGGAGT  GGAGACCAGA  TTTTGAGAGT  GAAAAGGTGA  AAATATCTCT  1260
ACAGTGCAAT  AGCACGAAAA  ACCTAACCTT  TGCAATGAGA  AGTTCAGGAG  ATTATGGAGA  1320
AGTAACGGGA  GCTTGGATAG  AGTTTGGATG  TCATAGAAAT  AAATCAAACC  TTCATACTGA  1380
AGCAAGGTTT  AGAATTAGAT  GTAGATGGAA  TGTAGGGAGT  GATACCTCGC  TCATTGATAC  1440
ATGTGGAAAC  ACTCCAAATG  TTTCAGGTGC  GAATCCTGTA  GATTGTACCA  TGTATTCAAA  1500
TAAAATGTAC  AAGTTTTCTT  TACCAAACGG  GTTTACAATG  AAGGTAGATG  ACCTTATTAT  1560
GCATTTCAAT  ATGCCAAAAG  CTGTAGAAAT  GAATAATATT  GCTGGAAATT  GGTCTTGTAC  1620
ATCTGACTTG  CCATCGTCAT  GGGGGTATAT  GAATTGTAAT  TGCCCAAATA  GTAGTAGTAG  1680
TTATAGTGGT  ACTAAAATGG  CATGTCCTAG  CAATCGAGGC  ATCTTAAGGA  ATTGGTATAA  1740
CCCAGTAGCA  GGATTACGAC  AATCCTTAGA  ACAGTATCAA  GTTGTAAAAC  AACCAGATTA  1800
CTTACTGGTC  CCAGAGGAAG  TCATGGAATA  TAAACCTAGA  AGGAAAAGGG  CAGCTATTCA  1860
TGTTATGTTG  GCTCTTGCAA  CAGTATTATC  TATTGCCGGT  GCAGGGACGG  GGGCTACTGC  1920
TATAGGGATG  GTAACACAAT  ACCACCAAGT  TCTGGCAACC  CATCAAGAAT  CTATGGAAAA  1980
GGTGACTGAA  GCCTTAGAGA  TAAACAACTT  AAGGTTAGTT  ACATTAGAGC  ATCAAGTACT  2040
AGTAATAGGA  TTAAAAGTAG  AAGCTATGGA  AAAATTTTTA  TATACAGCTT  TCGCTATGCA  2100
AGAATTAGGA  TGTAATCCAA  ATCAATTTTT  CTCCAAAATC  CCTCTTGAGT  TGTGGACAAG  2160
GTATAATATG  ACTATAAATC  AAACAATATG  GAATCATGGA  AATATAACTT  GGGGGAATG   2220
GTATAACCAC  ACCAAAGATT  TACAACCAAA  GTTTTATGAA  ATAATAATGG  ACATAGAACC  2280
AAATAATGTA  CAAGGGAAAA  CAGGGATACA  ACAATTACCC  AAGTGGGAAG  ATTGGGTAAG  2340
ATGGATAGGA  AATATTCCAC  AATATTTAAA  GGGACTATTG  GGAGGTATCT  TGGGAATAGG  2400
ATTAGGAGTG  TTATTATTGA  TTTTATGTTT  ACCTACATTG  GTTGATTGTA  TAAGAAATTG  2460
TATCCACAAG  ATACTAGGAT  ACACAGTAAT  TGCAATGCCT  GAAGTAGAAG  GAGAAGAAAT  2520
ACAACCACAA  ATGGAATTGA  GGAGAAATGG  TAGCCAATTT  GGCATGTCTG  AAAAAGAGGA  2580
GGAATGATGA  AGTATCTCAG  ACTTATTTTA  TAAGGGAGAT  ACTGTGCTAA  GTTCTTCCCT  2640
TTGAGGAAGG  TATGTCATAT  GAATCCATTT  CGAACCAAAT  CAAACTAATA  AGTATGTAT   2700
TGTAAGGTAA  AAGGAAAAGA  CAAAGAAGAA  GAAGAAAGAA  GAAAGCTTTC  AAGAGGATGA  2760
TGACAGAGTT  AGAAGATCGC  TTCAGGAAGC  TATTTGGCAC  GACTTCTACA  ACGGGAGACA  2820
GCACAGTAGA  TTCTGAAGAT  GAACCTCCTA  AAAAGAAAA   AAGGGTGGAC  TGGGATGAGT  2880
ATTGGAACCC  TGAAGAAATA  GAAAGAATGC  TTATGGACTA  GGGACTGTTT  ACGAACAAAT  2940
GATAAAAGGA  AATAGCTAAG  CATGACTCAT  AGTTAAAGCG  CTAGCAGCTG  CTTAACCGCA  3000
AAACCACATC  CTATGTAAAG  CTTGCTAATG  ACGTATAAGT  TGTTCCATTG  TAAGAGTATA  3060
```

-continued

| | | | | | | |
|---|---|---|---|---|---|---|
| TAACCAGTGC | TTTGTGAAAC | TTCGAGGAGT | CTCTCCGTTG | AGGACTTTCG | AGTTCTCCCT | 3120 |
| TGAGGCTCCC | ACAGATACAA | TAAATATTTG | AGATTGAACC | CTGTCAAGTA | TCTGTGTAAT | 3180 |
| CTTTTTTACC | TGTGAGGTCT | CGGAATCCGG | GCCGAGAACT | TCGCA | | 3225 |